US008110391B2

(12) United States Patent
Raven et al.

(10) Patent No.: US 8,110,391 B2
(45) Date of Patent: *Feb. 7, 2012

(54) DEGRADATION AND DETECTION OF TSE INFECTIVITY

(75) Inventors: Neil David Hammond Raven, Salisbury (GB); John Mark Sutton, Salisbury (GB)

(73) Assignee: Health Protection Agency, Salisbury, Wiltshire (GB)

( * ) Notice: Subject to any disclaimer, the term of this patent is extended or adjusted under 35 U.S.C. 154(b) by 1015 days.

This patent is subject to a terminal disclaimer.

(21) Appl. No.: 11/871,087

(22) Filed: Oct. 11, 2007

(65) Prior Publication Data

US 2008/0178306 A1 Jul. 24, 2008

Related U.S. Application Data

(63) Continuation of application No. 10/614,370, filed on Jul. 8, 2003, now Pat. No. 7,303,907.

(30) Foreign Application Priority Data

Jan. 8, 2001 (GB) .................................. 0100420.9
Feb. 26, 2001 (GB) .................................. 0104696.0
Jan. 8, 2002 (GB) ....................... PCT/GB02/00052
Jul. 11, 2002 (GB) .................................. 0216146.1

(51) Int. Cl.
C02F 3/34 (2006.01)
C12S 3/00 (2006.01)
C12S 9/00 (2006.01)
D06M 16/00 (2006.01)

(52) U.S. Cl. .................... 435/264; 435/262; 435/267
(58) Field of Classification Search .................. None
See application file for complete search history.

(56) References Cited

U.S. PATENT DOCUMENTS

| 4,597,762 A | 7/1986 | Walter et al. |
| 4,614,549 A | 9/1986 | Ogunbiyi et al. |
| 4,994,200 A | 2/1991 | Disch et al. |
| 5,182,204 A | 1/1993 | Estell et al. |
| 5,185,258 A | 2/1993 | Caldwell et al. |
| 5,192,677 A | 3/1993 | Kinsella et al. |
| 5,204,015 A | 4/1993 | Caldwell et al. |
| 5,223,166 A | 6/1993 | Disch et al. |
| 5,234,832 A | 8/1993 | Disch et al. |
| RE34,606 E | 5/1994 | Estell et al. |
| 5,700,676 A | 12/1997 | Bott et al. |
| 5,756,678 A | 5/1998 | Shenoy et al. |
| 5,763,257 A | 6/1998 | Bott et al. |
| 5,801,038 A | 9/1998 | Bott et al. |
| 5,810,944 A | 9/1998 | Smitkowski et al. |
| 5,977,324 A | 11/1999 | Prusiner et al. |
| 6,211,149 B1 | 4/2001 | Chesebro et al. |
| 6,312,936 B1 | 11/2001 | Poulose et al. |
| 6,613,505 B2 | 9/2003 | Shih |
| 7,303,907 B2 | 12/2007 | Raven et al. |
| 2005/0163776 A1 | 7/2005 | Raven et al. |
| 2008/0178306 A1 | 7/2008 | Raven et al. |
| 2009/0087877 A1 | 4/2009 | Hesp et al. |

FOREIGN PATENT DOCUMENTS

| AU | 742838 | 9/1998 |
| DE | 197 30 132 A1 | 2/1999 |
| EP | 0 251 446 | 1/1988 |
| EP | 0 328 299 | 8/1989 |
| EP | 1 251 138 | 10/2002 |
| EP | 0 723 590 | 12/2004 |
| EP | 1 526 182 | 4/2005 |
| FR | 2 867 388 | 3/2004 |
| WO | WO 89/06279 | 7/1989 |
| WO | WO 90/02562 | 3/1990 |
| WO | WO 95/10615 | 4/1995 |
| WO | WO 97/28192 | 8/1997 |
| WO | WO 97/38011 | 10/1997 |
| WO | WO 98/37210 | 8/1998 |
| WO | WO 00/22438 | 4/2000 |
| WO | WO 00/26238 | 5/2000 |
| WO | WO 00/29849 | 5/2000 |
| WO | WO 00/48003 | 8/2000 |
| WO | WO 00/78344 | 12/2000 |
| WO | WO 02/24871 A1 | 3/2002 |
| WO | WO 02/053723 | 7/2002 |
| WO | WO 02/083082 | 10/2002 |
| WO | WO 2005/092114 A2 | 10/2005 |

OTHER PUBLICATIONS

Buschmann, A., et al., "Cellular Prion Proteins of Mammalian Species Display an Intrinsic Partial Proteinase K Resistance," Biochem. Biophys. Res. Comm. 253:693-702, Academic Press (1998).

Kellershohn, N. and Laurent, M., "Species barrier in prion diseases: a kinetic interpretation based on the conformational adaption of the prion protein," Biochem. J. 334:539-545, Portland Press on behalf of the Biochemical Society (1998).

Perrett, S., et al., "Equilibrium Folding Properties of the Yeast Prion Protein Determinant Ure2," J. Mol. Biol. 290:331-345, Academic Press (1999).

Taylor, D.M., "Inactivation of Transmissble Degenerative Encephalopathy Agents: A Review," Vet. J. 159:10-17, Harcourt Publishers Ltd. (Jan. 2000).

Warwicker, J., "Species Barriers in a Model for Specific Prion Protein Dimerisation," Biochem. Biophys. Res. Comm. 232:508-512, Academic Press (1997).

International Search Report for International Patent Application No. PCT/GB02/00052, mailed Oct. 16, 2002.

O'Donohue, MJ., et al., "Cloning and expression in Bacillus subtilis of the npr gene from Bacillus thermoproteolyticus Rokko coding for the thermostable metalloprotease thermolysin", Biochem J., vol. 300, Pt. 2, pp. 599-603, Jun. 1994, (abstract).

Hicke, PM., et al., "Homoultimeric protease in the hyperthermophilic bacterium Thermotoga maritime has structural and amino acid sequence homology to bacteriocins in mesophilic bacteria", FEBS Lett., vol. 440, No. 3., pp. 393-398, Dec. 1998. (abstract).

(Continued)

Primary Examiner — Debbie K Ware
(74) Attorney, Agent, or Firm — Evan Law Group LLC

(57) ABSTRACT

A transmissible spongiform encephalopathy (TSE) agent is inactivated by exposing the TSE agent to a thermostable proteolytic enzyme at elevated temperature and at acid or alkaline pH. Following this step, or separately, presence of TSE infectivity is detected by detection of dimers of prion protein.

20 Claims, 25 Drawing Sheets

OTHER PUBLICATIONS

Sakamoto, S., et al., "Expression of aqualysin I (a thermophilic protease) in soluble form in *Escherichia coli* under a bacteriophage T7 prometer", Biosci Biotechnol Biochem., vol. 59, No. 8, pp. 1438-1443, Aug. 1995, (abstract).

Prusiner, Stanley B., et al., "Purification and Structural Studies of a Major Scrapie Prion Protein" Cell., vol. 38, pp. 127-134, Aug. 1984.

"Protease (Proteinase K) product description" Active Motif product profiles., http://www.activemotif.com/downloads/manual_pdfs/29012_Protease.pdf.,file creation date Mar. 8, 2002.

Daniel, R.M., et al., "Thermostable Proteases"., Biotechnology and Genetic Engineering Reviews, vol. 13, pp. 51-100, (1995).

Information in support of Notice of Opposition, against corresponding Australian Application, pp. 1-9, Oct. 14, 2005.

Information in support of Notice of Opposition, Amended, against corresponding Australian Application, pp. 1-17, Mar. 23, 2006.

McKinley, M.P., et al., "A protease-resistant protein is a structural component of the scrapie prion"., Cell, vol. 35, pp. 57-62, (1983).

McLeod, A.H., et al., "Proteolytic inactivation of the bovine spongiform encephalopathy agent"., Biochemical and Biophysical Research Communications, vol. 317, pp. 1165-1170, (2004).

Notice of Opposition to a European Patent, against corresponding European application, pp. 1-5, Jan. 9, 2006.

Opposition to European Patent No. 1 360 282 (corresponding European application), pp. 1-25, Jan. 9, 2006.

Peterson, M.E., et al., "A new intrinsic thermal parameter for enzymes reveals true temperature optima"., The Journal of Biological Chemistry, vol. 279, No. 20, Issue of May 14, pp. 20717-20722, (2004).

Product Description, "Protease (Proteinase K)", Active Motif, http://www.activemotif.com/catalog/molecular_biology/mtrap/components, 1 page, (2002).

Product Description, "Proteinase K", Worthington Biochemical Corporation, http://www.worthington-biochem.com/PROK/default.html, 4 pages, (publication date unknown).

Prusiner, S.B., et al., "Purification and structural studies of a major scrapie prion protein"., Cell, vol. 38, pp. 127-134, (1984).

Prusiner, S.B., et al., "Scrapie agent contains a hydrophobic protein"., Proc. Natl. Acad. Sci. USA, Biochemistry, vol. 78, No. 11, pp. 6675-6679, (1981).

Prusiner, S.B., et al., "Scrapie prions aggregate to form amyloid-like birefringent rods"., Cell, vol. 35, pp. 349-358, (1983).

Prusiner, S.B., et al., "Thiocyanate and hydroxyl ions inactivate the scrapie agent"., Proc. Natl. Acad. Sci. USA, Microbiology, vol. 78, No. 7, pp. 4606-4610, (1981).

Prusiner, S.B., et al., "Electrophoretic properties of the scrapie agent in agarose gels"., Proc. Natl. Acad. Sci. USA, Microbiology, vol. 77, No. 5, pp. 2984-2988, (1980).

Statutory Declaration of Victoria Alice Lawson, cited during opposition against corresponding European Patent Application, pp. 1-63, Dec. 13, 2005.

Statutory Declaration of Ronald Peter Weinberger cited during opposition against corresponding European Patent Application, pp. 1-46, Dec. 16, 2005.

Statutory Declaration of Khawar Sohail Siddiqui cited during opposition against corresponding European Patent Application, pp. 1-45, Nov. 29, 2005.

Taylor, D.M., "Inactivation of transmissible degenerative encephalopathy agents: A review"., The Veterinary Journal, vol. 159, No. 1, pp. 10-17, (2000).

Watson, J.D., et al., "Performing a polymerase chain reaction"., Recombinant DNA, Second Edition, Chapter 6, pp. 80-85, (1992).

Bajorath, J., et al., "The enzymatic activity of proteinase K is controlled by calcium"., European Journal of Biochemistry, vol. 176, pp. 441-447, (1988).

Bauer, C., et al., "Purification of a PrP-Dimer expressed in *E. coli*"., Infection, P-201, vol. 28, supplement No. 1, pp. 51, (2000).

Bernouli, C., et al., "Danger of accidental person-to-person transmission of creutzfeldt-jakob disease by surgery"., The Lancet, pp. 478-479, (1977).

Bolton, D.C., et al., "Identification of a protein that purifies with the scrapie prion"., Science, vol. 218, pp. 1309-1311, (1982).

Caughey, B., et al., "Scrapie infectivity correlates with converting activity, pretease resistance, and aggregation of scrapie-associated prion protein in guanidine denaturation studies"., Journal of Virology, vol. 71, No. 5, pp. 4107-4110, (1997).

Cho, H.J., "Requirement of a protein component for scrapie infectivity"., Intervirology, vol. 14, pp. 213-216, (1980).

Cho, H.J., "Inactivation of the scrapie agent by pronase"., Can. J. Comp. Med., vol. 47, pp. 494-496, (1983).

Ebeling, W., et al., "Proteinase K from Tritirachium album limber"., European Journal of Biochemistry, vol. 47, pp. 91-97, (1974).

Haki, G.D., et al., "Developments in industrially important thermostable enzymes: a review"., Bioresource Technology, vol. 89, pp. 17-34, (2003).

Herbert, R.A., "A perspective on the biotechnological potential of extremophiles"., Trends in Biotechnology, vol. 10, pp. 395-402, (1992).

Hunter, G.D., "The enigma of the scrapie agent: Biochemical approaches and the involvement of membranes and nucleic acids"., Slow transmissible diseases of the nervous system, eds: Prusiner & Hadlow, Academic Press, Inc., vol. 2, pp. 365-385, (1979).

Hunter, G.D., et al., "Attempts to release the scrapie agent from tissue debris"., J. Comp. Path., vol. 77, pp. 301-307, (1967).

Hunter, G.D., et al., "Further studies of the infectivity and stability of extracts and homogenates derived from scrapie affected mouse brains"., J. Comp. Path., vol. 79, pp. 101-108, (1969).

Kocisko, D.A., et al., "Cell-free formation of protease-resistant prion protein"., Nature, vol. 370, pp. 471-474, (1994).

Kristjansson, J.K., "Thermophilic organisms as sources of thermostable enzymes"., Trends In Biotechnology, vol. 7, pp. 349-353, (1989).

Laurenson, I.F., et al., "Contaminated surgical instruments and variant Creutzfeldt-Jakob disease"., The Lancet, vol. 354, pp. 1823, (1999).

Meyer, R.K., et al., "A monomer-dimer equilibrium of a cellular prion protein (PrP°) not observed with recombinant PrP"., The Journal of Biological Chemistry, vol. 275, No. 48, issue of Dec. 1, pp. 38081-38087, (2000).

Millson, G.C., et al., "The physico-chemical nature of the scrapie agent"., Slow virus diseases of animals and man, Chapter 11, edited by R.H. Kimberlin, North-Holland Publishing Company, pp. 243-266, (1976).

Ng, T.K., et al., "Industrial applications of thermostable enzymes"., Thermophiles: General, Molecular and Applied Microbiology, Brock TD Editor, John Wiley and Sons, chapter 9, pp. 197-215, (1986).

Priola, S.A., et al., "A 60-kDa prion protein (PrP) with properties of both the normal and scrapie-associated forms of PrP"., The Journal of Biological Chemistry, vol. 270, No. 7, Issue of Feb. 17, pp. 3299-3305, (1995).

Product Description, "Proteinase K", Fermentas Life Sciences, http://www.fermentas.com/profiles/modifyingenzymes/pdf/protk0491.pdf, 3 pages, (2004).

Sarath, G., et al., "Protease assay methods"., Proteolytic enzymes, Practical Approach, (ed. By Beynon, R.J., and Bond, J.S., Oxford University Press, New York, Oxford, pp. 25-55, (1989).

Prusiner, S.B., et al., "Further purification and characterization of scrapie prions"., Biochemistry, vol. 21, No. 26, pp. 6942-6950, (1982).

Prusiner, S.B., et al., "Gel electrophoresis and glass permeation chromatography of the hamster scrapie agent after enzymatic digestion and detergent extraction"., Biochemistry, vol. 19, No. 21, pp. 4892-4898, (1980).

Prusiner, S.B., et al., "Partial purification and evidence for multiple molecular forms of the scrapie agent"., Biochemistry, vol. 17, No. 23, pp. 4993-4999, (1978).

Sharp, R.J., et al., "Isolation and growth of hyperthermophiles"., Applied Microbial Physiology: A Practical Approach, Ch. 2, Eds. Stanbury and Rhodes, OUP, pp. 23-52, (1997).

Raymond, G.J., et al., "Molecular assessment of the potential transmissibilities of BSE and scrapie to humans"., Nature, vol. 388, pp. 285-288, (1997).

Rubenstein, R., et al., "Concentration and distribution of infectivity and $PrP^{Sc}$ following partial denaturation of a mouse adapted and a hamster-adapted scrapie strain"., Archives of Virology, vol. 139, pp. 301-311, (1994).

Safar, J., et al., "Molecular mass, biochemical composition, and physicochemical behavior of the infectious form of the scrapie precursor protein monomer"., Proc. Natl. Acad. Sci. USA, vol. 87, pp. 6373-6377, (1990).

Siezen, R.J., et al, "Homology modeling and protein engineering strategy of subtilases, the family of subtilisin-like serine proteinases"., Protein Engineering, vol. 4, No. 7, pp. 719-737, (1991).

Taylor, D.M., "Inactivation of prions by physical and chemical means"., Journal of Hospital Infection, vol. 43 (supplement), pp. S69-S76, (1999).

Taylor, D.M., et al., "Decontamination studies with the agents of bovine spongiform encephalopathy and scrapie"., Archives of Virology, vol. 139, pp. 313-326, (1994).

Wille, H., et al., "Separation of scrapie prion infectivity from PrP amyloid polymers"., J. Mol. Biol., vol. 259, pp. 608-621, (1996).

Corrected Evidence in Support, All opposition proceedings filed in corresponding Australian Opposition, Jan. 20, 2006.

Kascsak, R.J., et al., "Mouse polyclonal and monoclonal antibody to scrapie-associated fibril proteins"., Journal of virology, pp. 3688-3693, (1987).

Harmeyer, S., et al., "Synthetic peptide vaccines yield monoclonal antibodies to cellular and pathological prion proteins of ruminants"., Journal of General Virology, vol. 79, pp. 937-945, (1998).

Meyer, R.K., et al., "Detection of bovine spongiform encephalopathy-specific $PrP^{Sc}$ by treatment with heat and guanidine thiocyanate"., Journal of Virology, vol. 73, No. 11, pp. 9386-9392, (1999).

Wopfner, F., et al., "Analysis of 27 mammalian and 9 avian PrPs reveals high conservation of flexible regions of the prion protein"., Journal of Molecular Biology, vol. 289, pp. 1183-1178, (1999).

Dima, R.I., et al., "Exploring protein aggregation and self-propagation using lattice models: Phase diagram and kinetics"., Protein Science, vol. 11, pp. 1036-1049, (2002).

Abstract of: De Silva, B.S., et al., "Purified protein derivative (PPD) as an immunogen carrier elicits high antigen specificity to haptens"., Bioconjug Chemistry, vol. 10, No. 3, pp. 496-501, (1999).

Tompa, P., et al., "The role of dimerization in prion replication"., Biophysical Journal, vol. 82, pp. 1711-1718, (2002).

Bickel, U., et al., "Delivery of peptides and proteins through the blood-brain barrier"., Advanced Drug Delivery Reviews, vol. 46, pp. 247-279, (2001).

Abstract of: Lussow, A.R., et al., "Mycobacterial heat-shock proteins as carrier molecules"., European Journal of Immunology, vol. 21, No. 10, pp. 2297-2302, (1991).

Abstract of: Belhadj, J.B., et al., "Antigenicity of linear and cyclic peptides mimicking the disulfide loops in HIV-2 envelope glycoprotein: synthesis, reoxidation and purification"., Journal of Peptide Research, vol. 51, No. 5, pp. 370-385, (1998).

Abstract of: Patel, G., et al., "A cyclic peptide analogue of the loop III region of platelet-derived growth factor-BB is a synthetic antigen for the native protein"., Journal of Peptide Research, vol. 53, No. 1, pp. 68-74, (1999).

Riley, M.L., et al., "High-level expression and characterization of a glycosylated covalently linked dimer of the prion protein"., Protein Engineering, vol. 15, No. 6, pp. 529-537, (2002).

Abstract of: Ibsen, P.H., et al., "Induction of polyclonal antibodies to the S1 subunit of pertussis toxin by synthetic peptides coupled to PPD: effect of conjugation method, adjuvant, priming and animal species"., APMIS, vol. 100, No. 2, pp. 159-169, (1992).

Handbook of proteolytic enzymes, AJ Barret, ND Rawlings and FF Woessner Jr., eds., Academic Press, San Diego, chapter 106, 1998.

Source book of enzymes, JS White and D. Chong White, CRC Press, p. 573, 1997.

Zobeley, et al., "Infectivity of scrapie prions bound to a stainless steel surface", Molecular Medicine, 5, pp. 240-243, 1999.

Flechsig, et al., "Transmission of scrapie by steel-surface-bound prions", Molecular Medicine, 7, pp. 679-684.

Ahring, B.K., "Perspectives for Anaerobic Digestion", Advances in Biochemical Engineering/Biotechnology, vol. 81, pp. 1-30, (2003).

Antloga, K. et al., "Prion Disease and Medical Devices", ASAIO Journal 2000, 46, (6), pp. S69-S72, (2000).

Axon, A.T.R. et al., "Variant Creutzfeldt-Jakob Disease (vCJD) and Gastrointestinal Endoscopy", Endoscopy, 33, (12), pp. 1070-1080, (2001).

Bolton, D.C. et al., "Molecular Characteristics of the Major Scrapie Prion Protein", Biochemistry, 23, pp. 5898-5906, (1984).

Fichet, G. et al., "Novel methods for disinfection of prion-contaminated medical devices", Lancet, vol. 364, pp. 521-526, (2004).

Hsiao, K.K. et al., "Serial transmission in rodents of neurodegeneration from transgenic mice expressing mutant prion protein", Proc. Natl. Acad. Sci., vol. 91, pp. 9126-9130, (1994).

Hui, Z. et al., Alkaline serine protease produced by Streptomyces sp. Degrades $PrP^{Sc}$, Biochemical and Biophysical Research Communications, 321, pp. 45-50, (2004).

Jackson, G.S. et al., "An enzyme-detergent method for effective prion decontamination of surgical steel", Journal of General Virology, 86, pp. 869-878, (2005).

Langeveld, J.P.M. et al., "Enzymatic Degradation of Prion Protein in Brain Stem from Infected Cattle and Sheep", The Journal of Infectious Diseases, 188, pp. 1782-1789, (2003).

Lawson, V.A. et al., "Enzymatic detergent treatment protocol that reduces protease-resistant prion protein load and infectivity from surgical-steel monofilaments contaminated with human-derived prion strain", Journal of General Virology, 88, pp. 2905-2914, (2007).

Lemmer, K. et al., "Decontamination of surgical instruments from prion proteins: in vitro studies on the detachment, destabilization and degradation of $PrP^{Sc}$ bound to steel surfaces", Journal of General Virology, 85, pp. 3805-3816, (2004).

Lin, X. et al., Expression of the *Bacillus licheniformis* PWD-1 keratinase gene in *B. subtilis*, Journal of Industrial Microbiology & Biotechnology, 19, pp. 134-138, (1997).

Marsh, R.F. et al., "Physical and Chemical Properties of the Transmissible Mink Encephalopathy Agent", Journal of Virology, vol. 3, No. 2, pp. 176-180, (1969).

McDonnell, G. et al. "The Challenge of Prion Decontamination", Clinical Infectious Diseases, 36, pp. 1152-1154, (2003).

Müller, H. et al., "Influence of Water, Fat, and Glycerol on the Mechanism of Thermal Prion Inactivation", The Journal of Biological Chemistry, vol. 282, No. 49, pp. 35855-35867, (2007).

Müller-Hellwig, S. et al., "Biochemical evidence for the proteolytic degradation of infectious prion protein $PrP^{Sc}$ in hamster brain homogenates by foodborne bacteria", Systematic and Applied Microbiology, 29, pp. 165-171, (2006).

Peretz, D. et al., "Inactivation of Prions by Acidic Sodium dodecyl Sulfate", Journal of Virology, vol. 80, No. 1, pp. 322-331, (2006).

Prusiner, S.B., "Prions", Proc. Natl. Acad. Sci. *USA*, vol. 95, pp. 13363-13383, (1998).

Rutala, W.A. et al., "Creutzfeldt-Jakob Disease: Recommendations for Disinfection and Sterilization", Healthcare Epidemiology, 32, pp. 1348-1356, (2001).

Safar, J.G. et al., "Measuring prions causing bovine spongiform encephalopathy or chronic wasting disease by immunoassays and transgenic mice", Nature Biotechnology, vol. 20, pp. 1147-1150, (2002).

Safar, J.G. et al., "Diagnosis of human prion disease", PNAS, vol. 102, No. 9. pp. 3501-3506, (2005).

Taylor, D.M., "Resistance of Transmissible Spongiform Encephalopathy Agents to Decontamination", Medicine and Public Health System, vol. 7, pp. 58-67, (2001).

Taylor, D.M., "Resistance of Transmissible Spongiform Encephalopathy Agents to Decontamination", Medicine and Public Health System, vol. 11, pp. 136-145, (2004).

Telling, G.C. et al., "Interactions between wild-type and mutant prion proteins modulate neurodegeneration in transgenic mice", Genes & Development, 10, pp. 1736-1750, (1996).

Tsiroulnikov, K. et al., "Hydrolysis of the Amyloid Prion Protein and Nonpathogenic Meat and Bone Meal by Anaerobic Thermophillic Prokaryotes and *Streptomyces* Subspecies", Journal of Agricultural and Food Chemistry, 52, pp. 6353-6360, (2004).

Voorhorst, W.G.B. et al., "Homology modeling of two subtilisin-like serine proteases from the Hyperthermophilic archaea *Pyrococcus furiosus* and *Thermococcus stetten*", Protein Engineering, vol. 10, No. 8, pp. 905-914, (1997).

Voorhorst, W.G.B. et al., "Isolation and Characterization of the Hyperthermostable Serine Protease, Pyrolysin, and Its Gene from the Hyperthermophilic Archaeon *Pyrococcus furiosus*", The Journal of Biological Chemistry, vol. 271, No. 34, pp. 20426-20431, (1996).

Will, R.G., "Acquired prion disease: iatrogenic CJD, variant CJD, kuru", British Medical Bulletin, 66, pp. 255-265, (2003).

Yoshioka, M. et al., "Characterization of a proteolytic enzyme derived from a *Bacillus* strain that effectively degrades prion protein", Journal of Applied Microbioloby, 102, pp. 509-515, (2007).

Yoshioka, M. et al., "Assessment of Prion Inactivation by Combined Use of *Bacillus*-Derived Protease and SDS", Biosci. Biotechnol. Biochem, 71, (10), pp. 2565-2568, (2007).

International Search Report or Declaration for International application No. PCT/GB03/01295, dated Mar. 20, 2003.

GB Search Report for Application No. GB 0206584.5, dated Oct. 16, 2002.

Alonso, D.O.V. et al., "Mapping the early steps in the pH-induced conformational conversion of the prion protein," Proc. Natl. Acad. Sci. USA, 98, pp. 2985-2989, (2001).

Anon. "Update: Creutzfeldt-Jakob disease in a patient receiving a cadaveric dura mater graft". MMWR, 36, pp. 324-325, (1987).

Bernoulli, C. et al., "Danger of accidental person-to-person transmission of Creutzfeldt-Jakob disease by surgery", Lancet. 309, pp. 478-479, (1977).

Bordier, C. "Phase separation of integral membrane proteins in Triton X-114 solution", J Biol Chem., 256 ,4, pp. 1604-1607, (1981).

Bolton, D.C. et al., "Identification of a protein that purifies with the scrapie prion", Science, 218, pp. 1309-1311, (1982).

Brooke, F.J. et al., "Lyodura use and the risk of iatrogenic Creutzfeldt-Jakob disease", in Australia Med J Aust., 180, pp. 177-181, (2004).

Brown, P. et al., "Iatrogenic Creutzfeldt-Jakob disease at the millennium", Neurology, 55, pp. 1075-1081, (2000).

Bruce, M.E. et al., "Transmissions to mice indicate that 'new variant' CJD is caused by the BSE agent", Nature, 389, pp. 498-501, (1997).

Bruce, M.E. et al., "Strain characterization of natural sheep scrapie and comparison with BSE," J Gen Virol, 83, pp. 695-704, (2002).

Caughey, B. et al., "Scrapie Infectivity Correlates with Converting Activity, Protease Resistance, and Aggregation of Scrapie-Associated Prion Protein in Guanidine Denaturation Studies", J. Virol., 71, pp. 4107-4110, (1997).

Cho, H.J., "Inactivation of the scrapie agent by pronase", Can. J. Comp. Med., 47, pp. 494-496, (1983).

Collins, S. et al., "Surgical treatment and risk of sporadic Creutzfeldt-Jakob disease: a case-control study", Lancet., 353, pp. 693-697, (1999).

Croes, E.A. et al., "Creutzfeldt-Jakob disease 38 years after diagnostic use of human growth hormone", Neurol Neurosurg Psychiatry, 72, pp. 792-793, (2002).

De Silva, B.S. et al., "Purified Protein Derivative (PPD) as an Immunogen Carrier Elicits High Antigen Specificity to Haptens", Bioconjug Chem., 10, pp. 496-501, (1999).

Diringer, H. et al., "Scrapie infectivity, fibrils and low molecular weight protein", Nature, 306, pp. 476-478, (1983).

Glatzel, M. et al., "Extraneural Pathologic Prion Protein in Sporadic Creutzfeldt-Jakob Disease", N Engl J Med. 349, pp. 1812-1820, (2003).

Grobben, A.H. et al., "Inactivation of the bovine spongiform encephalopathy (BSE) agent by the acid and alkaline processes used in the manufacture of bone gelatine", Biotechnol. Appl. Biochem., 39, pp. 329-338, (2004).

Herzog, C. et al., "Tissue distribution of bovine spongiform encephalopathy agent in primates after intravenous or oral infection", Lancet., 363, pp. 422-428, (2004).

Hill, A.F. et al., "The same prion strain causes vCJD and BSE", Nature., 389, pp. 448-450, (1997).

Hill A.F. et al., "Subclinical prion infection," Trends in Microbiol., 11, pp. 578-584, (2003).

Hilton, D.A. et al., "Accumulation of prion protein in tonsil and appendix: review of tissue samples", BMJ, 325, pp. 633-634, (2002).

Joiner, S. et al., "Irregular presence of abnormal prion protein in appendix in variant Creutzfeldt-Jakob disease", J. Neurol. Neurosurg. Psychiatry, 73, pp. 597-598, (2002).

Klohn, P.C. et al., "A quantitative, highly sensitive cell-based infectivity assay for mouse scrapie prions", Proc Natl Acad Sci USA, 100,20, pp. 11666-11671, (2003).

Kocisko, D.A. et al., "Cell-free formation of protease-resistant prion protein", Nature, 370, pp. 471-474, (1994).

Langeveld, J.P. et al., "Enzymatic Degradation of Prion Protein in Brain Stem from Infected Cattle and Sheep", J. Inf. Dis., 188, pp. 1782-1789, (2003).

Llewelyn, C.A. et al., "Possible transmission of variant Creutzfeldt-Jakob disease by blood transfusion", Lancet., 363, pp. 417-221, (2004).

Naslaysky, N. et al., "Sphingolipid Depletion Increases Formation of the Scrapie Prion Protein in Neuroblastoma Cells Infected with Prions," J. Biol. Chem., 274, pp. 20763-20771, (1999).

Peden, A.H. et al., "Preclinical vCJD after blood transfusion in a PRNP codon 129 heterozygous patient", Lancet., 364, pp. 527-529, (2004).

Prusiner, S.R., "Novel proteinaceous infectious particles cause scrapie", Science, 216, pp. 136-144, (1982).

Ritchie, D.L. et al., "Advances in the detection of prion protein in peripheral tissues of variant Creutzfeldt-Jakob disease patients using paraffin-embedded tissue blotting", Neuropathology & Applied Neurobiology, 30, pp., 360-368, (2004).

Rubenstein, R et al., "Concentration and distribution of infectivity and $PrP^{Sc}$ following partial denaturation of a mouse-adapted and a hamster-adapted scrapie strain", Arch. Virol., 139, pp. 301-311, (1994).

Safar, J. et al., "Eight prion strains have $PrP^{Sc}$ molecules with different conformations", Nat Med, 4, 10, pp. 1157-1165, (1998).

Safar, J. et al., "Subcellular distribution and physicochemical properties of scrapie-associated precursor protein and relationship with scrapie agent", Neurology, 40, pp. 503-508, (1990).

Schwab, M et al. "Amplified DNA with limited homology to myc cellular oncogene is shared by human neuroblastoma cell lines and a neuroblastoma tumour", Nature, 305, pp. 245-248, (1983).

Swerdlow, A.J. et al., "Creutzfeldt-Jakob disease in United Kingdom patients treated with human pituitary growth hormone", Neurology, 61, pp. 783-791, (2003).

Taylor, D.M. et al., "Decontamination studies with the agents of bovine spongiform encephalopathy and scrapie," Arch. Virol., 139, pp. 313-326, (1994).

Taylor, D.M., "Inactivation of transmissible degenerative encephalopathy agents: A review", Vet J., 159, pp. 10-17, (2000).

Taylor, D.M., "Transmissible degenerative encephalopathies: Inactivation of the unconventional causal agents, in: Principles and practice of disinfection, preservation and sterilization", A.D. Russell, W.B. Hugo and G.A.J. Ayliffe (Eds.) Blackwell Scientific Publications, Oxford, pp. 222-236, (1999).

Taylor, D.M., "Resistance of transmissible spongiform encephalopathy agents to decontamination", Contrib. Microbiol., 7, pp. 58-67, (2001).

Taylor, D.M. et al., "Thermostability of mouse-passaged BSE and scrapie is independent of host PrP genotype: implications for the nature of the causal agents", J. Gen. Virol., 83, pp. 3199-3294, (2002).

Taylor, D.M., "Resistance of transmissible spongiform encephalopathy agents to decontamination", Contrib Microbiol., 11, pp. 136-145, (2004).

van der Werf, S. et al., "Ability of linear and cyclic peptides of neutralization antigenic site 1 of poliovirus type 1 to induce virus cross-reactive and neutralizing antibodies", Res Virol., 145, pp. 349-359, (1994).

Ward, H.J.T. et al., "Sporadic Creutzfeldt-Jakob disease and surgery: a case-control study using community controls", Neurology, 59, pp. 543-548, (2002).

Wells, G.A.H., "Pathology of Nonhuman Spongiform Encephalopathies: Variations and their Implications for Pathogenesis", Dev. Biol. Stand., 80, pp. 61-69, (1993).

Will, R.G., "Epidemiology of Creutzfeldt-Jacob disease", Br. Med. Bull., 49, pp. 960-970, (1993).

Wille, J.H. et al., "Separation of Scrapie Prion Infectivity from PrP Amyloid Polymers", Mol. Biol., 259, pp. 608-621, (1996).

Rutala, W.A. et al., "Creutzfeldt-Jakob disease: recommendations for disinfection and sterilization", Clin Infect Dis., 32, pp. 1348-1356, (2001).

Weber D.J. et al., "Managing the risk of nosocomial transmission of prion diseases", Curr Opin Infect Dis., 15, pp. 421-425, (2002).

Yan Z.X. et al., "Infectivity of Prion Protein Bound to Stainless Steel Wires: a Model for Testing Decontamination Procedures for Transmissible Spongiform Encephalopathies", Infect Control Hosp Epidemiol., 25, pp. 280-283, (2004).

Zou W.Q. et al., "Acidic pH and detergents enhance in vitro conversion of human brain $PrP^C$ to a $PrP^{Sc}$-like form", J. Biol. Chem., 277, pp. 43942-43947, (2002).

International Search Report dated May 23, 2007 for PCT application No. PCT/GB2007/000630.

Ferrier, B. et al., "Cells release in association with exosomes," PNAS, vol. 101, No. 26, pp. 9683-9688, (2004).

Porto-Carreiro, I. et al., "Prions and exosomes: From PrPc trafficking to PrPsc propagation," Blood Cells, Molecules, and Diseases, 35, pp. 143-148, (2005).

Safar, J.G. et al., "Diagnosis of human prion disease," PNAS, vol. 102, No. 9, pp. 3501-3506, (2005).

International Search Report dated Jun. 20, 2006 for PCT application No. GV0603775.8.

Fevrier, B. et al., "Exosomes: A Bubble Ride for Prions?," Traffic, vol. 6, pp. 10-17, (2005).

Raymond, G.J. et al., "Inhibition of Protease-Resistant Prion Formation in a Transformed Deer Cell Line Infected with Chronic Wasting Disease," Journal of Virology, vol. 80, pp. 596-604, (2006).

Taylor, D.M., "Inactivation of Transmissible Degenerative Encephalopathy Agents: A Review", The Veterinary Journal, vol. 159, pp. 10-17, (2000).

Lanes 1 & 10, marker proteins
Lane 2, untreated mbh
Lane 3, 50°C
Lane 4, 60°C
Lane 5, 70°C
Lane 6, 80°C
Lane 7, 90°C
Lane 8, 100°C
Lane 9, Protease M Lanes 1 & 10, marker proteins
Lane 2, untreated mbh
Lane 3, pH2
Lane 4, pH4
Lane 5, pH6
Lane 6, pH8
Lane 7, pH10
Lane 8, pH12
Lane 9, Protease M Lanes 1 & 10, marker proteins
Lane 2, untreated mbh
Lanes 3 - 8, Rokko digest (20mg.ml$^{-1}$ - 0.1 mg.ml$^{-1}$)
Lane 9, Rokko (1mg.ml$^{-1}$)

Lanes 1 & 9, marker proteins
Lane 2, untreated mbh
Lane 3, 2% SDS
Lane 4, 1% SDS
Lane 5, 0.5% SDS
Lane 6, 0.25% SDS
Lane 7, mbh + 2% SDS
Lane 8, Rokko (20mg.ml$^{-1}$)

Lanes 1 & 10, marker proteins
Lanes 2 & 3, mbh
Lanes 4 - 6, mbh pellet
Lanes 7 - 9, mbh supernatant Lanes 1 & 10, marker proteins
Lanes 2 & 3, mbh
Lanes 4 - 6, mbh pellet
Lanes 7 - 9, mbh supernatant Lanes 1 & 10, marker proteins
Lane 2, untreated mbh
Lane 3, Protease G digest
Lane 4, Protease G
Lane 5, Protease R digest
Lane 6, Protease R
Lane 7, Protease C digest
Lane 8, Protease C
Lane 9, rec. mouse PrP Lanes 1 & 10, marker proteins
Lane 2, untreated mbh
Lane 3, Protease G digest
Lane 4, Protease G
Lane 5, Protease R digest
Lane 6, Protease R
Lane 7, Protease C digest
Lane 8, Protease C
Lane 9, rec. mouse PrP

```
                                                              50                        60
         Ala  Gly  Gly  Ala  Ser  Val  Pro  Ser  Glu  Thr  Met  Val  Pro  Asn  Asp  Asn  Ser  His  Gly  Thr  His  Val  Ala
 549     GCA  GGC  GGA  GCC  AGC  GTT  CCT  TCT  GAA  ACA  ATG  GTT  CCT  AAT  GAC  AAC  TCT  CAC  GGA  ACT  CAC  GTT  GCC 70                                           80                                    90
         Gly  Thr  Val  Ala  Ala  Leu  Asn  Asn  Ser  Ile  Gly  Val  Leu  Gly  Val  Ala  Pro  Ser  Ala  Ser  Leu  Tyr  Ala  Val  Lys
 624     GGC  ACA  GTT  GCG  GCT  CTT  AAT  AAC  TCA  ATC  GGT  GTA  TTA  GGC  GTT  GCC  CCA  AGC  GCA  TCA  CTT  TAC  GCT  GTA  AAA 100                                               110
         Asp  Ala  Met  Asn  Ser  Gly  Val  Val  Val  Val  Val  Ala  Gly  Gln  Tyr  Ser  Trp  Ile  Ile  Glu  Asn  Ala  Ser  Asn  Met
 699     GAC  GCT  ATG  AAC  AGC  GGT  GTC  GTT  GTT  GTA  GCT  GGC  CAA  TAC  AGC  TGG  ATC  ATT  CAG  AAC  GCG  ATC  AAT  ATG 120                                    130                                  140
         Asp  Val  Ile  Asn  Met  Ser  Leu  Gly  Gly  Pro  Ser  Gly  Ser  Ala  Ala  Leu  Lys  Ala  Ala  Val  Asp  Lys  Ala  Val  Ala
 774     GAC  GTT  ATT  AAC  ATG  AGC  CTC  GGC  GGT  CCT  TCT  GGT  TCT  GCG  GCT  TTA  AAA  GCG  GCA  GTT  GAT  AAA  GCG  GTT  GCA

Ser  Gly  Val  Val  Val  Val  Ala  Ala  Ala  Ala  Gly  Asn  Glu  Gly  Ser  Ser  Gly  Ser  Thr  Ser  Thr  Val  Gly  Tyr  Pro  Gly
 849     TCC  GGC  GTA  GTC  GTT  GTT  GCA  GCC  GCA  GGT  AAC  GAA  GGC  ACT  TCC  GGC  AGC  ACA  AGC  ACA  GTC  GGA  TAC  CCT  GGT 170                                  180                                     190
         Lys  Tyr  Pro  Ser  Val  Ile  Ala  Val  Gly  Ala  Val  Asp  Ser  Ser  Asn  Gln  Arg  Ala  Ser  Phe  Ser  Ser  Val  Gly  Pro
 924     AAA  TAC  CCT  TCT  GTC  ATT  GCA  GTA  GGT  GCT  GTT  GAC  AGC  AGC  AAC  CAA  AGA  GCA  TCT  TTC  TCA  AGC  GTA  GGA  CCT 200                                     210
         Glu  Leu  Asp  Val  Met  Ala  Pro  Gly  Val  Ser  Ile  Gln  Ser  Thr  Leu  Pro  Gly  Asn  Lys  Tyr  Gly  Ala  Tyr  Asn  Gly
 999     GAG  CTT  GAT  GTC  ATG  GCA  CCT  GGC  GTA  TCT  ATC  CAA  AGC  ACG  CTT  CCT  GGA  AAC  AAA  TAC  GGG  GCG  TAC  AAC  GGT 220                                  230                                     240
         Thr  Ser  Met  Ala  Ser  Pro  His  Val  Ala  Gly  Ala  Ala  Ala  Leu  Ile  Leu  Ser  Lys  His  Pro  Asn  Trp  Thr  Asn  Thr  Gly
 1074    ACG  TCA  ATG  GCA  TCT  CCG  CAC  GTT  GCC  GGA  GCG  GCT  GCG  CTT  ATT  CTT  TCT  AAG  CAC  CCG  AAC  TGG  ACA  AAC  ACT
```

```
                                                                    260                           270
      Gln Val Arg Ser Ser Ser Leu Glu Asn Thr Thr Thr Lys Leu Gly Asp Ser Phe Tyr Tyr Gly Lys Leu Ile Asn
1149  CAA GTC CGC AGC AGT AGC TTA GAA AAC ACC ACT ACA AAA CTT GGT GAT TCT TTC TAC TAT GGA AAA GGG CTG ATC AAC
                   275
      Val Gln Ala Ala Ala Gln OC
1224  GTA CAG GCG GCA GCT CAG TAA AACATAAAAAACCGGCCTTGCCCTCCCCATGTTCAATCCGCTCC
                                                 TERM
1316  ATAATCGACGGATGGCTCCCTCTGAAAATTTTAACCAGAACGCCCGGTTGACCCCGGTCAGTCCCGCTCAGTCCTGAAACGTCTCAATCGCCG

1416  CTTCCCCGGTTCCGGTCAGCTCAATGCCGTAACGGTCGGCCCGCGTTTCCTGATACCGGGAGACGGCATTCGTAATCCGATC
```

Fig. 13.B3

Fig. 14
CONSERVED RESIDUES IN SUBTILISINS FROM *BACILLUS AMYLOLIQUEFACIENS*

Comparison of subtilisin sequences from:
B. amyloliquefaciens   B. subtilis   B. licheniformis   B. lentus

Initial evaluation results

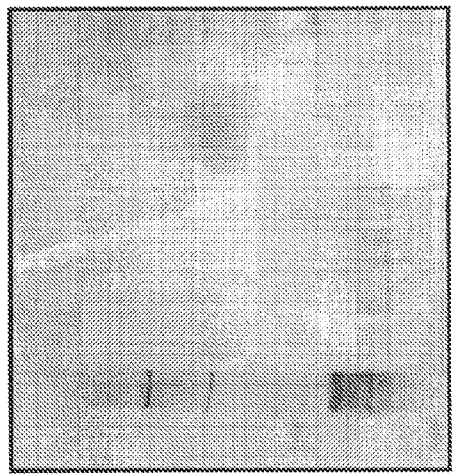
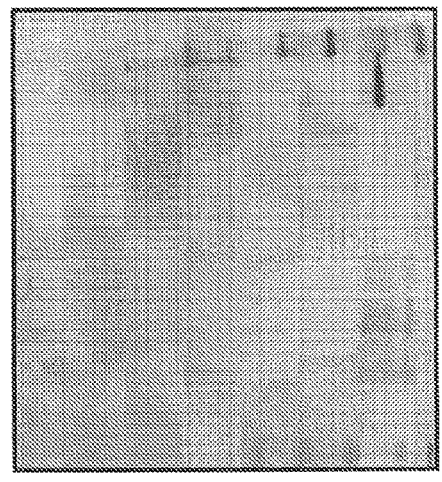
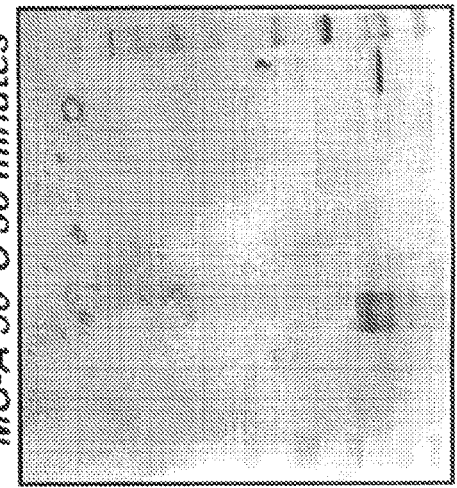
Fig. 17
Comparison with Properase

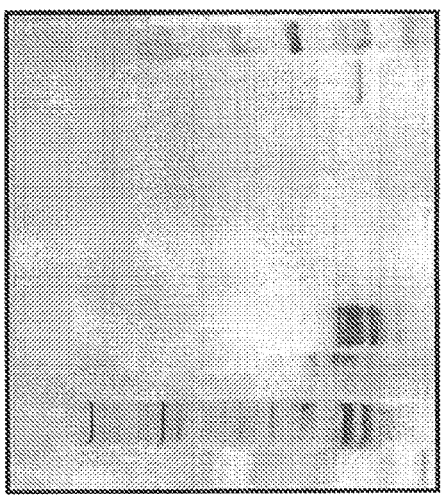
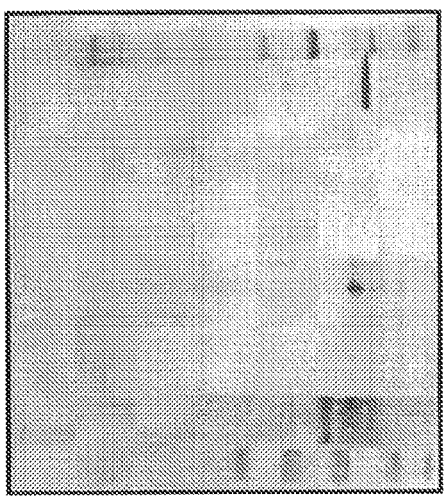
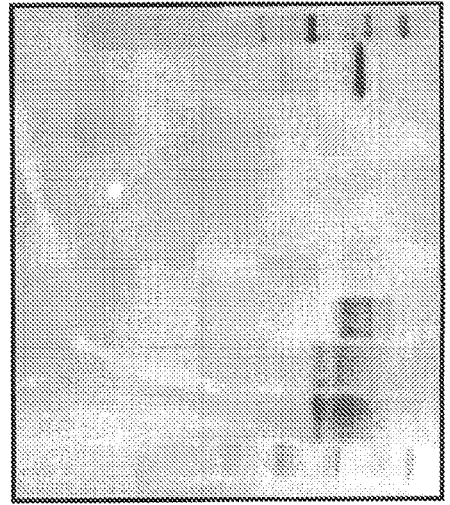
Fig. 18
Comparison with Properase

Fig. 19
Temperature profiling with MC-3
50°C 30 minutes
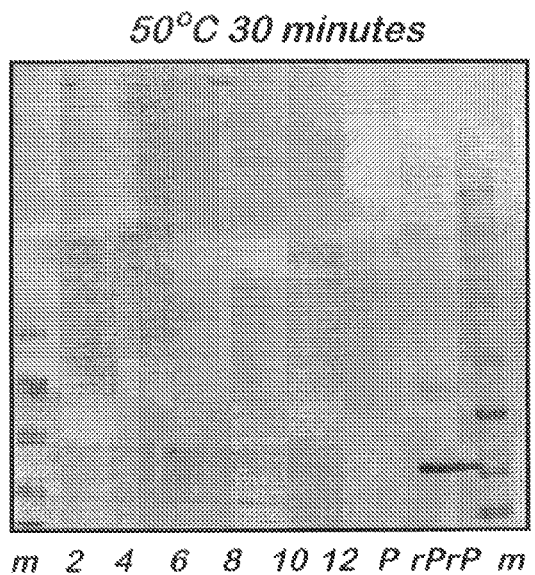
m  2  4  6  8  10 12  P  rPrP  m
70°C 30 minutes
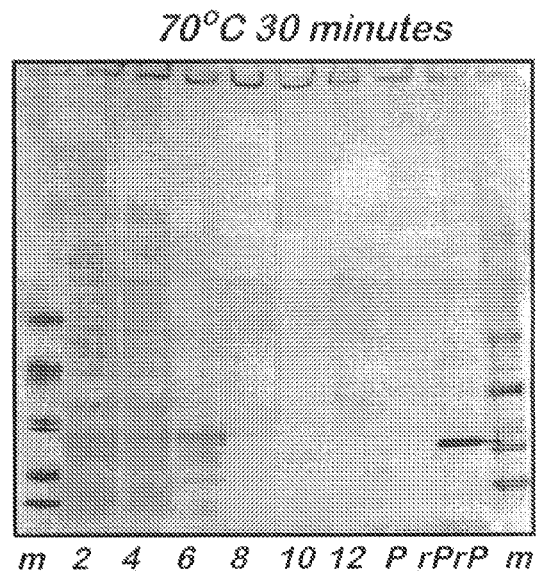
m  2  4  6  8  10 12  P  rPrP  m
60°C 30 minutes
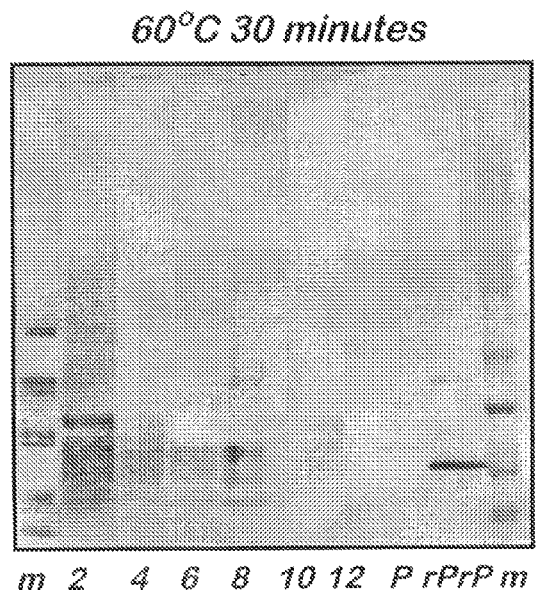
m  2  4  6  8  10 12  P  rPrP  m
80°C 30 minutes
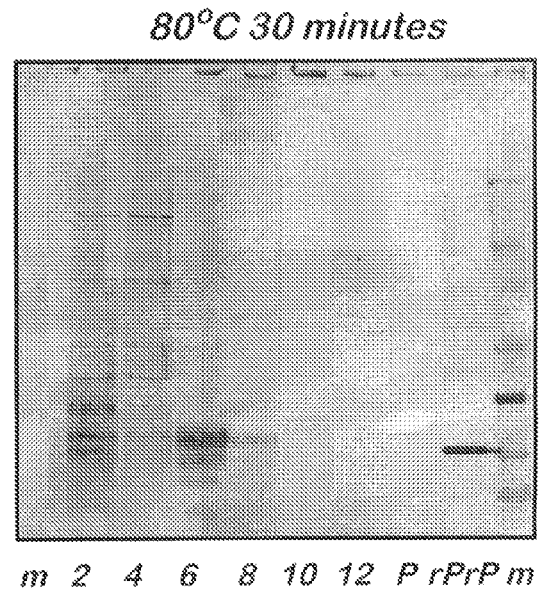
m  2  4  6  8  10 12  P  rPrP  m Detection with PAb2
mbh pH 2-12 digested at 50 °C 30 minutes

Fig. 21
MC-3 dilutions at pH10 & pH12
pH 10
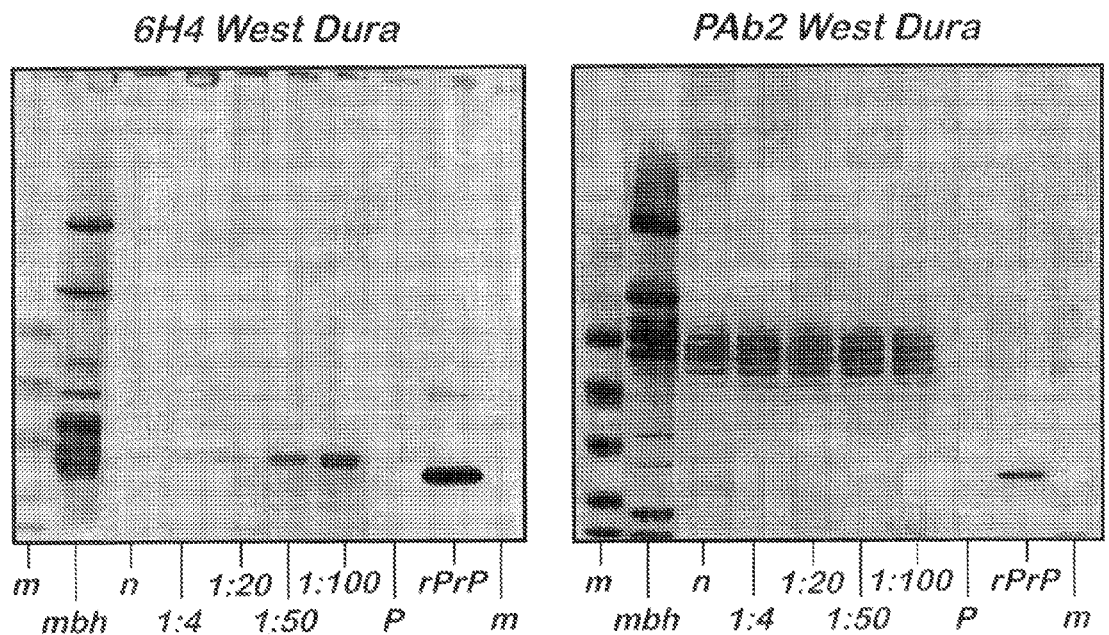
pH 12
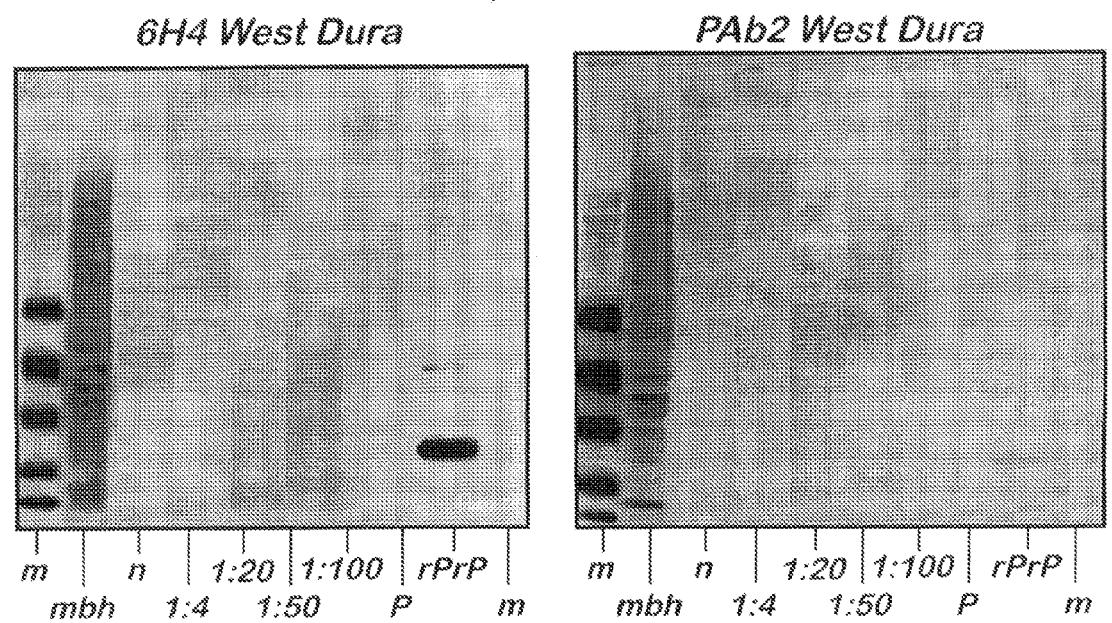

*Comparison with Proteinase K*

Characteristic PrPSc monomer bands pH 2-10
Incomplete digestion pH12 however no clear monomers
HMW bands present pH 2-12

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Cys Gly Gly Trp Gly Gln Pro His Gly Gly Cys
1               5                   10

<210> SEQ ID NO 2
<211> LENGTH: 23
<212> TYPE: PRT
<213> ORGANISM: Artificial Sequence
<220> FEATURE:
<223> OTHER INFORMATION: Synthetic

<400> SEQUENCE: 2

Cys Gly Gly Tyr Met Leu Gly Ser Ala Met Ser Arg Pro Ile Ile His
1               5                   10                  15

Phe Gly Asn Asp Tyr Glu Cys
            20

<210> SEQ ID NO 3
<211> LENGTH: 25
<212> TYPE: PRT
<213> ORGANISM: Artificial Sequence
<220> FEATURE:
<223> OTHER INFORMATION: Synthetic

<400> SEQUENCE: 3

Cys Val Asn Ile Thr Ile Lys Gln His Thr Val Thr Thr Thr Thr Lys
1               5                   10                  15

Gly Glu Asn Phe Thr Glu Thr Asp Cys
            20                  25

<210> SEQ ID NO 4
<211> LENGTH: 19
<212> TYPE: PRT
<213> ORGANISM: Artificial Sequence
<220> FEATURE:
<223> OTHER INFORMATION: Synthetic

<400> SEQUENCE: 4

Cys Ile Thr Gln Tyr Gln Arg Glu Ser Gln Ala Tyr Tyr Gln Arg Gly
1               5                   10                  15
```

Ala Ser Cys

<210> SEQ ID NO 5
<211> LENGTH: 1497
<212> TYPE: DNA
<213> ORGANISM: Bacillus amyloliquefaciens

<400> SEQUENCE: 5

| | | | | |
|---|---|---|---|---|
| ggtctactaa | aatattattc | catactatac | aattaataca | cagaataatc | tgtctattgg | 60 |
| ttattctgca | aatgaaaaaa | aggagaggat | aaagagtgag | aggcaaaaaa | gtatggatca | 120 |
| gtttgctgtt | tgctttagcg | ttaatcttta | cgatggcgtt | cggcagcaca | tcctctgccc | 180 |
| aggcggcagg | gaaatcaaac | ggggaaaaga | aatatattgt | cgggtttaaa | cagacaatga | 240 |
| gcacgatgag | cgccgctaag | aagaaagatg | tcatttctga | aaaaggcggg | aaagtgcaaa | 300 |
| agcaattcaa | atatgtagac | gcagcttcag | tcacattaaa | cgaaaaagct | gtaaaagaat | 360 |
| tgaaaaaaga | cccgagcgtc | gcttacgttg | aagaagatca | cgtagcacat | gcgtacgcgc | 420 |
| agtccgtgcc | ttacggcgta | tcacaaatta | agcccctgc | tctgcactct | caaggctaca | 480 |
| ctggatcaaa | tgttaaagta | gcggttatcg | acagcggtat | cgattcttct | catcctgatt | 540 |
| taaaggtagc | aagcggagcc | agcatggttc | cttctgaaac | aaatcctttc | caagacaaca | 600 |
| actctcacgg | aactcacgtt | gccggcacag | ttgcggctct | taataactca | atcggtgtat | 660 |
| taggcgttgc | gccaagcgca | tcactttacg | ctgtaaaagt | tctcggtgct | gacggttccg | 720 |
| gccaatacag | ctggatcatt | aacggaatcg | agtgggcgat | cgcaaacaat | atggacgtta | 780 |
| ttaacatgag | cctcggcgga | ccttctggtt | ctgctgcttt | aaaagcggca | gttgataaag | 840 |
| ccgttgcatc | cggcgtcgta | gtcgttgcgg | cagccggtaa | cgaaggcact | tccggcagct | 900 |
| caagcacagt | gggctaccct | ggtaaatacc | cttctgtcat | tgcagtaggc | gctgttgaca | 960 |
| gcagcaacca | aagagcatct | ttctcaagcg | taggacctga | gcttgatgtc | atggcacctg | 1020 |
| gcgtatctat | ccaaagcacg | cttcctggaa | acaaatacgg | ggcgtacaac | ggtacgtcaa | 1080 |
| tggcatctcc | gcacgttgcc | ggagcggctg | ctttgattct | ttctaagcac | ccgaactgga | 1140 |
| caaacactca | agtccgcagc | agtttagaaa | acaccactac | aaaacttggt | gattctttgt | 1200 |
| actatggaaa | agggctgatc | aacgtacaag | cggcagctca | gtaaaacata | aaaaaccggc | 1260 |
| cttggccccg | ccggtttttt | attattttc | ttcctccgca | tgttcaatcc | gctccataat | 1320 |
| cgacggatgg | ctccctctga | aaattttaac | gagaaacggc | gggttgaccc | ggctcagtcc | 1380 |
| cgtaacggcc | aactcctgaa | acgtctcaat | cgccgcttcc | cggtttccgg | tcagctcaat | 1440 |
| gccataacgg | tcggcggcgt | tttcctgata | ccgggagacg | gcattcgtaa | tcggatc | 1497 |

<210> SEQ ID NO 6
<211> LENGTH: 382
<212> TYPE: PRT
<213> ORGANISM: Bacillus amyloliquefaciens

<400> SEQUENCE: 6

Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

```
Gly Lys Val Gln Lys Gln Phe Lys Tyr Val Asp Ala Ser Val Thr
 65                  70                  75                  80

Leu Asn Glu Lys Ala Val Lys Glu Leu Lys Lys Asp Pro Ser Val Ala
                 85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Ser Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Leu
        355                 360                 365

Tyr Tyr Gly Lys Gly Leu Ile Asn Val Gln Ala Ala Ala Gln
    370                 375                 380

<210> SEQ ID NO 7
<211> LENGTH: 275
<212> TYPE: PRT
<213> ORGANISM: Bacillus amyloliquefaciens

<400> SEQUENCE: 7

Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
             20                  25                  30

Ser Gly Ile Asp Ser Ser His Pro Asp Leu Lys Val Ala Gly Gly Ala
         35                  40                  45

Ser Met Val Pro Ser Glu Thr Asn Pro Phe Gln Asp Asn Asn Ser His
     50                  55                  60
```

Gly Thr His Val Ala Gly Thr Val Ala Leu Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Val Asp Lys Ala Val Ala
    130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Gln Asn Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
        275

<210> SEQ ID NO 8
<211> LENGTH: 275
<212> TYPE: PRT
<213> ORGANISM: Bacillus subtilis

<400> SEQUENCE: 8

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Asp Lys Ala Val Ser
    130                 135                 140

Ser Gly Ile Val Val Ala Ala Ala Gly Asn Glu Gly Ser Ser Gly
145                 150                 155                 160

```
Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
                260                 265                 270

Ala Ala Gln
        275

<210> SEQ ID NO 9
<211> LENGTH: 274
<212> TYPE: PRT
<213> ORGANISM: Bacillus licheniformis

<400> SEQUENCE: 9

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255
```

Gly Ser Ser Phe Tyr Tyr Gly Lys Gly Leu Ile Asn Val Glu Ala Ala
            260                 265                 270

Ala Gln

<210> SEQ ID NO 10
<211> LENGTH: 269
<212> TYPE: PRT
<213> ORGANISM: Bacillus lentus

<400> SEQUENCE: 10

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 11
<211> LENGTH: 275
<212> TYPE: PRT
<213> ORGANISM: Artificial Sequence
<220> FEATURE:
<223> OTHER INFORMATION: Bacillus subtilis

<400> SEQUENCE: 11

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
 50                  55                  60

Gly Thr His Val Ala Gly Thr Ile Ala Ala Leu Asp Asn Ser Ile Gly
 65                  70                  75                  80

Val Leu Gly Val Ser Pro Ser Ala Ser Leu Tyr Ala Val Lys Val Leu
                85                  90                  95

Asp Ser Thr Gly Ser Gly Ala Ile Ser Trp Ile Ile Asn Gly Ile Glu
                100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
            130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
                260                 265                 270

Ala Ala Gln
        275

<210> SEQ ID NO 12
<211> LENGTH: 269
<212> TYPE: PRT
<213> ORGANISM: Artificial Sequence
<220> FEATURE:
<223> OTHER INFORMATION: Bacillus lentus

<400> SEQUENCE: 12

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg G

-continued

```
Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Pro Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

DEGRADATION AND DETECTION OF TSE INFECTIVITY

CROSS REFERENCE TO RELATED APPLICATION

This application is a continuation application of U.S. application Ser. No. 10/614,370, filed Jul. 8, 2003, entitled "Degradation and Detection of TSE Infectivity," now U.S. Pat. No. 7,303,907.

The invention is in the field of methods and compositions for the sterilisation of materials and apparatus that may have been contaminated with infectious agents and for detection of those agents. In particular, the invention relates to methods for the inactivation and detection of transmissible spongiform encephalopathy (TSE) agents and provides compositions for degrading and detecting TSE located on or within infected materials.

Transmissible spongiform encephalopathies (TSEs) are a group of fatal neurological diseases that include Creutzfeld-Jacob disease (CJD) and Kuru in humans, bovine spongiform encephalopathy (BSE) in cattle and Scrapie in sheep. TSEs are characterised by the conversion of a normal host protein into a pathogenic protein within the brain tissue of an infected animal. The pathogenic form of protein is often referred to as a prion and is highly resistant to physical and chemical degradation. The prion is believed to be the transmissive agent through which the TSE disease is passed on between animals.

There has been considerable public alarm in recent years over the risks associated with consumption of meat products, and especially beef, potentially infected with BSE, the bovine form of TSE. Much of this concern is associated with the belief that the BSE prion when eaten by a human may in some cases cause the incurable human form of the disease, referred to as variant CJD (vCJD). Rigorous practices have been adopted in the agricultural and meat rendering industries to reduce the risk of cross contamination between BSE infected carcasses and meat that is destined for human consumption or other animal derived products such as tallow. However, BSE infected animals can still be unintentionally processed in abattoirs, especially if the animal is in the early stages of the disease and therefore undetected as an infected TSE host. There is also a considerable risk in disposal of known BSE infected material, particularly if the equipment used in the disposal operation is then reused in normal rendering practices without adequate sterilisation.

Sterilisation of instruments and equipment following potential exposure to TSE infected tissue is of primary importance. In particular, surgical equipment such as scalpels, forceps and endoscopes should be thoroughly sterilised before use on patients to avoid disease transmission.

It has been reported that the CJD infectious agent was accidentally transferred on surgical electrodes, inserted into the brain of a human patient with CJD, to two other previously uninfected patients (Bernouli et al (1977) The Lancet i: pp 478-479). The electrodes concerned were sterilised with ethanol and formaldehyde vapour between each procedure, conditions previously thought to be sufficient to eliminate virtually all infectious agents, and yet the CJD infectious agent was able to withstand such harsh conditions and infect the recipient patients' brain tissue.

TSE transmission is typically observed in cases where infected material is transferred between animals or implanted into an animal. As described previously, incomplete or inadequate sterilisation of surgical instruments can lead to such transfer of infected material between patients. Even the most rigorous chemical cleaning and steam sterilisation procedures can fail to remove blood and tissue from surgical instruments, especially in the jaws or joints of forceps and clamps (Laurenson (1999) The Lancet, 20 November). Thus, the risk of unintentional TSE transfer can be unnecessarily high.

TSE agents, or prions, are known to be highly resistant to denaturation and degradation, more so than would normally be expected for a protein. Taylor (J. Hosp. Infect. (1999) 43 supplement, pp S69-76) reviews a number of methods for inactivating prion proteins.

Chemical methods for inactivating TSE prion proteins include treatment of infected material with sodium hydroxide or sodium hypochlorite solutions (Taylor et al. (1994) Arch. Virol. 139, pp 313-326), although infectivity of the prion is shown to survive exposure to 2M sodium hydroxide for up to two hours.

Alternative methods for inactivating TSE prions include autoclaving, but again BSE and scrapie agent has been shown to survive treatment at 134-138° C. for 18 minutes (Taylor et al. ibid). Thus, a combined chemical/heating approach has been proposed in which infected materials are exposed to 1M sodium hydroxide followed by autoclaving at 121° C. for between 30 and 60 minutes (Taylor, J. Hosp. Infect. (1999) 43 supplement, pp S69-76). This combined method has shown that inactivation of TSE infectious agents can be achieved, albeit under very harsh conditions.

However, many materials, such as plastics, polymers and non-protein animal derivatives, cannot be exposed to such extreme conditions without themselves being destroyed. The chemical and physical processes described above are only really suitable for sterilising metal instruments and surgical tools that are not too large in size and which can fit inside a standard autoclave. More delicate instruments such as endoscopes cannot be exposed to extreme conditions of high temperature without the risk of permanent damage to their internal components.

Further, chemical processes typically involve the use of caustic and/or chaotropic agents which are hazardous to handle and dispose of. It would, therefore, be desirable to provide a method for inactivating agents such as TSE without the need to use large amounts of hazardous substances and which method could be scaled up for use on larger objects and areas as well as on smaller objects.

Taylor (Vet. J. (2000) 159 pp 10-17) describes tests using proteolytic enzymes to deactivate prion proteins. Proteases such as trypsin have little effect in non-denaturing conditions (Taylor (2000) p. 14) but other proteases such as proteinase K may have an effect on TSE infectivity following prolonged digestion times. However, the majority of current TSE inactivation methods are aimed towards chemical and physical degradation procedures.

It is an object of the invention, therefore, to provide methods and means for effectively inactivating TSE infectious agents under conditions that can be readily applied to a variety of locations and situations. It is a further object of the invention to reduce the need for extreme conditions of very high temperature and harsh chemical denaturants in order to inactivate TSE agents located on or within TSE infected materials.

A first aspect of the invention provides a method for inactivating a TSE agent comprising exposing the TSE agent to a thermostable proteolytic enzyme.

The methods and compositions of the invention are suitable for the inactivation of TSE agent in apparatus and materials infected or suspected as being infected with TSE agent. Medical apparatus is taken to include any item that is in use for surgery, either as an in-patient or out/day patient, dentistry/orthodontics, ophthalmology, gynaecology, obstetrics, veterinary practice, chiropody, audiology, general practice, tattooing. This would include, but not be limited to the following:

items of small equipment such as scalpels, clamps, forceps, retractors, burrs, probes, needles, picks, scissors, drills, drill bits, chisels, dissectors, rasps, osteotomes, chisels, reamers, curettes, dissectors, shears, suction tubes, scissors, rongeurs, instrument pins, laryngeal mirrors, lead hands, ring cutters, saws, dentist's drills, mirrors, electrodes, irrigation handsets, facoemulsification handsets, larger equipment such as endoscopes, laparoscopic instruments, tonometers and other instruments used in invasive procedures, furniture such as operating tables, dentist's chairs, lighting, anaesthetic equipment that might be exposed to body tissue during operations, and equipment such as steam autoclaves, portable autoclaves, porous load sterilisers, sonicators, dishwashers, ultrasonic cleaners, drying racks.

Surfaces such as operating theatre walls and floors would also be treated with formulations based on the invention.

The method of the invention is also suitable for routine decontamination of instruments and facilities used for slaughter, meat handling, meat rendering, food preparation and associated processes. These would include, but not be limited to, the following:

small equipment such as knives, axes, meat hooks, hand saws, mechanical saws, cleavers, larger equipment such as mincers, dicers, rendering equipment, butchers blocks, and facilities such as slaughterhouses, butchers, rendering plants.

In addition, the methods and compositions of the invention are suitably used in a prophylactic or precautionary mode, where definite knowledge of infection is uncertain. For example, the method of the invention can be easily incorporated into the standard sterilisation protocols used for preparation of surgical apparatus prior to use its use in surgical procedures.

The methods and compositions of the present invention are also suitably used for the inactivation of TSE agents in potentially contaminated clinical waste and culled animal material. At present, this waste material is incinerated at 1000° C., which requires specialised facilities and is expensive. It is an advantage of the present invention that a TSE inactivation procedure can occur at temperatures and in conditions which do not require highly specialised facilities and that the prospects of complete inactivation of the TSE agent are comparable to the more energy intensive and expensive incineration procedures.

The term transmissible spongiform encephalopathy (TSE) agent is intended to encompass all neurological diseases that are apparently transmitted via a pathogenic prion protein intermediate. Such TSEs typically include the human diseases Creutzfeld-Jacob disease (CJD), variant Creutzfeld-Jacob disease (vCJD), Kuru, fatal familial insomnia and Gerstmann-Straussler-Scheinker syndrome. Non-human TSEs include bovine spongiform encephalopathy (BSE), scrapie, feline spongiform encephalopathy, chronic wasting disease, and transmissible mink encephalopathy. Given that vCJD is currently understood to be a human form of BSE, it is apparent that certain TSE agents are capable of crossing the species barrier and that novel TSEs from non-bovine sources could become evident in future.

The proteolytic enzyme of the invention is typically a protease but can be suitably any biological polymeric molecule capable of catalysing cleavage of a polypeptide chain.

It is a feature of the invention that the proteolytic enzyme is a thermostable enzyme, that is, that it demonstrates optimal biological activity at temperatures in excess of the normal mammalian body temperature of 37° C. In embodiments of the invention the enzyme is thermally stable and biologically active, and inactivation is carried out, at temperatures equal to or greater than 40° C.; preferably in the range of 50° C. to 120° C.; and more preferably where the temperature is between 55° C. and 85° C. In a specific embodiment of the invention the temperature is about 60° C. In a further specific embodiment the temperature is about 80° C.

Thermostable proteolytic enzymes suitable for use in the methods and compositions of the invention are obtainable from a number of sources such as thermophilic bacteria and archaea. In one embodiment of the present invention the thermostable proteolytic enzyme is isolated from thermophilic bacteria, hyperthermophilic bacteria and archaea. Suitable organisms for extraction of proteolytic enzymes for use in the invention include *Thermotoga maritima; Thermotoga neopolitana; Thermotoga thermarum; Fervidobacterium islandicum; Fervidobacterium nodosum; Fervidobacterium pennivorans; Thermosipho africanus; Aeropyrum pernix; Thermus flavus; pyrococcus* spp.; *Sulfolobus solfataricus; Desulfurococcus; Bacillus thermoproteolyticus; Bacillus stearo-thermophilus; Bacillus* sp. 11231; *Bacillus* sp. 11276; *Bacillus* sp. 11652; *Bacillus* sp. 12031; *Thermus aquaticus; Thermus caldophilus; Thermus* sp. 16132; *Thermus* sp. 15673; and *Thermus* sp. Rt41A.

The aforementioned organisms are not the only sources of thermostable proteases. Indeed, some organisms that are not considered to be truly thermophilic can also express thermostable proteolytic enzymes. Such organisms are commonly termed thermodurable in that although they do not choose to live in conditions of high temperature, they can withstand high temperatures for limited periods. A number of *Bacillus* species fall in the category of thermodurability and are known to produce thermostable subtilisin-type proteases.

The pH at which the inactivation is performed can range from acid to alkaline, but is typically in the region of pH 8-13, preferably pH greater than 9 and more preferably around pH 12. Similarly, the thermostable protease is active in a pH range from acid to alkaline, but typically is optimally active in the region of pH 8-13, and preferably pH greater than 9 and more preferably around pH 12.

In an example of the invention in use, the proteolytic enzyme is extracted from a culture of the thermophilic bacteria or archaea. The culture is suitably maintained under the optimal conditions for the organism typically within a bioreactor. Thus, a continuous source of the organism can be maintained, allowing proteolytic enzyme to be obtained whenever needed.

Alternatively, in an example of the invention in use described in more detail below, the gene encoding a thermostable proteolytic enzyme is isolated from the source organism, *Bacillus thermoproteolyticus*. The gene is used to generate a recombinant expression construct, typically a plasmid, which is transformed into a host organism, *Escherichia coli*. The transformed *E. coli* is grown in a bioreactor and when at an appropriate cell density the expression of the plasmid construct is initiated and the proteolytic enzyme harvested using standard methods. The recombinant expression route allows for the production of the proteolytic enzyme product under less extreme conditions of temperature than would be required for the original source organism.

The recombinant route is further advantageous in that it allows for the genetic manipulation of recombinant thermostable protease genes in order to increase thermal stability or biological activity or for some other purpose. Thus, the activity of a thermostable proteolytic enzyme can be readily optimised for use in the methods and compositions of the invention.

Proteases are proteolytic enzymes that are carbonyl hydrolases which generally act to cleave peptide bonds of proteins or peptides. As used herein, "protease" means a naturally-occurring protease or a recombinant protease. Naturally-occurring proteases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

The present invention includes the use of protease enzymes, for example naturally occurring carbonyl hydrolases or non-naturally occurring carbonyl hydrolase variants (protease variants). The protease enzymes useful in this invention exhibit a greater hydrolytic activity than proteinase K. In the context of this invention, the hydrolytic activity of the subtilisins was measured and comparable assays include, but are not limited to those described in Proteolytic enzymes, Practical Approach (Ed. by Beynon, R J and Bond, J S, Oxford University Press, New York, Oxford, pp. 25-55 (1989); and the digestion of PrP-res proteins (Raymond, et al, Nature, 388:285-288 (1997). For example, the enzymatic activity of subtilisins could also be measured by using chromogenic substrates. Incubation of proteases with these substrates could result in the cleavage of the substrate and liberation of p-nitroaniline that is detected spectrophotometrically at 405 nm. Other exemplary methods of analyzing the subtilisins are by using the substrate N-succinyl-Ala-Ala-Pro-Phe-p-nitroanilide (0.8 mM in 20 mM sodium phosphate buffer, pH 8.5 or 0.8 mM in 20 mM Britton-Robinson buffer, pH 8.5). The incubation is carried out at 25° C. and followed spectrophotometrically for 4 min. The concentration of the protease is chosen so that the liberation of p-nitroaniline is linear during the whole analysis.

Proteases useful in the practice of this invention include all those disclosed in U.S. Pat. No. 6,312,936, the contents of which are hereby incorporated by reference, e.g. those proteases found in Bacillus amyloliquefaciens (SEQ. ID NO:7), Bacillus subtilis (SEQ. ID. NO:8), Bacillus licheniformis (SEQ.ID.NO:9) and Bacillus lentus (SEQ.ID.NO:10). Another Bacillus lentus useful in the practice of this invention is the DSM 5483. The hydrolase variants may also have a different proteolytic activity, stability, substrate specificity, pH profile and/or performance characteristic as compared to the precursor carbonyl hydrolase from which the amino acid sequence of the variant is derived. Specifically, such protease variants have an amino acid sequence not found in nature, which is derived by substitution of a plurality of amino acid residues of a precursor protease with different amino acids. The precursor protease may be a naturally-occurring protease or a recombinant protease.

The protease variants useful herein encompass the substitution of any of the nineteen naturally occurring L-amino acids at the designated amino acid residue positions. Such substitutions can be made in any precursor subtilisin (procaryotic, eucaryotic, mammalian, etc.). Throughout this application reference is made to various amino acids by way of common one- and three-letter codes. Such codes are identified in Dale, M. W. (1989), *Molecular Genetics of Bacteria*, John Wiley & Sons, Ltd., Appendix B.

The protease variants useful herein are preferably derived from a *Bacillus subtilisin*. More preferably, the protease variants are derived from *Bacillus amyloliquefaciens* subtilisin, *Bacillus lentus* subtilisin and/or subtilisin 309.

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include but are not limited to the subtilisins identified in FIG. 15 herein. Generally and for purposes of the present invention, numbering of the amino acids in proteases corresponds to the numbers assigned to the mature *Bacillus amyloliquefaciens* subtilisin sequence presented in FIG. 13.

"Recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. No. RE 34,606, U.S. Pat. No. 5,204,015 and U.S. Pat. No. 5,185,258, U.S. Pat. No. 5,700,676, U.S. Pat. No. 5,801,038, and U.S. Pat. No. 5,763,257.

"Non-human subtilisins" and the DNA encoding them may be obtained from many procaryotic and eucaryotic organisms. Suitable examples of procaryotic organisms include gram negative organisms such as *E. coli* or *Pseudomonas* and gram positive bacteria such as *Micrococcus* or *Bacillus*. Examples of eucaryotic organisms from which subtilisin and their genes may be obtained include yeast such as *Saccharomyces cerevisiae*, fungi such as *Aspergillus* sp.

A "protease variant" has an amino acid sequence which is derived from the amino acid sequence of a "precursor protease". The precursor proteases include naturally-occurring proteases and recombinant proteases. The amino acid sequence of the protease variant is "derived" from the precursor protease amino acid sequence by the substitution, deletion or insertion of one or more amino acids of the precursor amino acid sequence. Such modification is of the "precursor DNA sequence" which encodes the amino acid sequence of the precursor protease rather than manipulation of the precursor protease enzyme per se. Suitable methods for such manipulation of the precursor DNA sequence include methods disclosed herein, as well as methods known to those skilled in the art (see, for example, EP 0 328299, WO89/06279 and the U.S. patents and applications already referenced herein).

In a preferred embodiment of the invention, the protease is a subtilisin derived from a *Bacillus* species, to include, but not limited to B. subtilis, B. lentus, B. licheniformis and B. amyloliquefaciens.

In a further embodiment, the protease is a *Bacillus lentus* subtilisin having mutations N76D, S103A and V104I described previously in WO 95/10615 and identified specifically in that patent as SEQ. ID. NO. 12 and shown in FIG. 7.

In a preferred embodiment, the protease used for inactivation of TSE agents on surgical instruments or in waste animal material is a modified *Bacillus subtilis* subtilisin having equivalent amino acid changes to those described for the *Bacillus lentus* subtilisin variant; specifically amino acid changes N76D, S103A and V104I. This protease is referred to as MC-3 in Examples 3 and 4 below.

In a further embodiment, the subtilisin used for the inactivation of TSE was the subtilisin from *Bacillus licheniformis* referred to as MC-4 in Examples 3 and 4 below. Equivalent mutations to those described for *Bacillus subtilis* and *Bacillus lentus* subtilisins would also be valuable reagents for inactivation of TSEs. Similarly, the subtilisin from *B. amyloliquefaciens* (often referred to as BPN') carrying mutations N76D, S103A and V104I is also a suitable protease for these applications.

One embodiment of the present invention utilizes protease variants having at least one modification of an amino acid position corresponding to positions 27, 76, 87, 101, 103, 104, 123, 159, 222, 232, 236, 245, 248, 252, and 274 of *Bacillus amyloliquefaciens* subtilisin. Exemplary embodiments and/or combinations contemplated by the inventors include Y217L; K27R/V104Y/N123S/T274A; N76D/S103A/V104I; S101G/S103A/V104I/G159D/A232V/Q236H/Q245R/N248D/N252K. Other embodiments include at least one modification of the precursor protease made to at least one position corresponding to positions 120, 167, 170, 194, 195, and 235 of *Bacillus amyloliquefaciens*. Exemplary embodiments include combinations selected from G195E/M222A; M222S; Y167A/R170S/A194P; D36_N76D/H120D/G195E/K235N. Still another embodiment includes at least one modification at an amino acid position corresponding to positions selected from the group consisting of 3, 4, 99, 101, 103, 104, 159, 194, 199, 205, 217 of *Bacillus lentus*. Exemplary embodiments include combinations selected from S99D/S101R/S103A/V104I/G159S; S99D/S101R/S103A/V104I/G159S/S3T/V4I/A194P/V199M/V205I/L217D and S99D/S101R/S103A/V104I/G159S/S3T/V4I/V205I/L217D of a mature *Bacillus lentus* DSM 5483 alkaline protease. These amino acid position numbers refer to those assigned to the mature *Bacillus amyloliquefaciens* subtilisin sequence presented in FIG. 13. The invention, however, is not limited to the mutation of this particular subtilisin but extends to precursor proteases containing amino acid residues at positions which are "equivalent" to the particular identified residues in *Bacillus amyloliquefaciens* subtilisin. In a preferred embodiment of the present invention, the precursor protease is selected from a *Bacillus amyloliquefaciens* or a *Bacillus lentus* subtilisin, the substitutions are made at the equivalent amino acid residue positions in *B. lentus* corresponding to those listed above.

A residue (amino acid) position of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor protease is directly compared to the *Bacillus amyloliquefaciens* subtilisin primary sequence and particularly to a set of residues known to be invariant in subtilisins for which sequence is known. For example, FIG. 14 herein shows the conserved residues as between *B. amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained. Siezen et al. (1991) *Protein Eng.* 4(7):719-737 shows the alignment of a large number of serine proteases. Siezen et al. refer to the grouping as subtilases or subtilisin-like serine proteases.

For example, in FIG. 15, the amino acid sequence of subtilisin from *Bacillus amyloliquefaciens, Bacillus subtilis, Bacillus licheniformis (carlsbergensis)* and *Bacillus lentus* are aligned to provide the maximum amount of homology between amino acid sequences. A comparison of these sequences shows that there are a number of conserved residues contained in each sequence. These conserved residues (as between BPN' and *B. lentus*) are identified in FIG. 14.

These conserved residues, thus, may be used to define the corresponding equivalent amino acid residues of *Bacillus amyloliquefaciens* subtilisin in other subtilisins such as subtilisin from *Bacillus lentus* (PCT Publication No. WO89/06279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 15A and 15B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis*.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of the precursor protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protease in question to the *Bacillus amyloliquefaciens* subtilisin. The best model is the crystallographic model giving the lowest R factor for experimental diffraction data at the highest resolution available.

$$R \text{ factor} = \frac{\sum_h \_Fo(h)\_ - \_Fc(h)\_}{\sum_h \_Fo(h)\_}$$

Equivalent residues which are functionally analogous to a specific residue of *Bacillus amyloliquefaciens* subtilisin are defined as those amino acids of the precursor protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution are conserved residues whereas others are not. In the case of residues which are not conserved, the substitution of one or more amino acids is limited to substitutions which produce a variant which has an amino acid sequence that does not correspond to one found in nature. In the case of conserved residues, such substitutions should not result in a naturally-occurring sequence. The protease variants of the present invention include the mature forms of protease variants, as well as the pro- and prepro-forms of such protease variants. The prepro-forms are the preferred construction since this facilitates the expression, secretion and maturation of the protease variants.

A second aspect of the invention provides for a method of sterilising apparatus, comprising the step of exposing the apparatus to a solution comprising a thermostable proteolytic enzyme.

The term "sterilising" is commonly understood to mean the procedure by which living organisms are removed from or killed in a substrate, such as a piece of equipment or a solution. In the present case the TSE agent, or prion, is not technically considered to be a living organism, in the sense that a bacterium or virus is, because it does not apparently contain any genetic material. However, the transmission of the TSE pathogenic agent between animals does result in disease. Thus, the term "sterilising" as used herein is applied to the procedure by which both pathogenic agents (such as TSE agents) and living organisms are rendered non-infective or removed from or killed in a substrate.

In a preferred embodiment, the method of the invention comprises maintaining the sterilising solution at a temperature below 100° C., preferably at least 45° C. and more preferably between 45° C. and 85° C. The pH of the sterilising solution can range from acid to alkaline, but is typically in the region of pH 8-13, at least pH 9 and more preferably around pH 12. Similarly, the thermostable protease is active in a pH range from acid to alkaline, but typically is optimally active in the region of pH 8-13, at least pH9 and more preferably around pH 12.

In specific embodiments of the invention the sterilising solution is applied to the apparatus as a spray. The advantage of this mode of application is that, larger surface areas of apparatus, operating tables or even walls of rooms (for example in abattoirs) can be treated with the sterilising solution of the invention. Typically the solution will be heated to an optimal temperature, for example between 60° C. to 80° C., before being sprayed onto the surface that is to be sterilised, that surface being optionally heated in advance.

Alternatively, the apparatus is immersed in the sterilising solution for a predetermined period of time. Again, the temperature of the solution is typically optimised prior to immersion of the contaminated apparatus. It is optional to include ultrasonication means in the immersion bath to enable ultrasonic cleaning to occur at the same time as treatment with the sterilising solution of the invention.

In a third aspect, the invention provides for a method of sterilising material, comprising exposing said material to a first solution comprising a thermostable proteolytic enzyme; and then exposing the apparatus to at least a second solution comprising a second thermostable proteolytic enzyme. In use, the material is typically apparatus, surgical or meat rendering equipment, or TSE infected biological waste.

By dividing the sterilisation method into at least two, and optionally more, successive steps the conditions in each step can be optimised to ensure maximum inactivation of any TSE agent present. Thus, the temperatures and/or pH of successive steps can be different. In specific embodiments of the invention the proteolytic enzymes in the first and second (and optionally more) solutions are the same, or are different.

In a fourth aspect the invention provides for a composition for inactivating a TSE agent, comprising a thermostable proteolytic enzyme.

Typically, the composition of the invention further comprises a buffering agent. In a specific embodiment of the invention the buffering agent has a $pK_a$ of between 8 and 13. Alkaline buffers suitable for use in the method of the invention include 4-cyclohexylamino-1-butanesulfonic acid (CABS) which has a pKa of 10.7 at 25° C., and 3-cyclohexylamino-1-propanesulfonic acid (CAPS) which has a pKa of 10.4 at 25° C.

Alternatively, the composition of the invention comprises sufficient sodium hydroxide or other alkaline agent to adjust the pH of the composition to alkaline, preferably to at least pH 9 and more preferably around pH 12. Addition of 1M sodium hydroxide to the composition of the invention, using a pH probe calibrated using Universal standards, is generally sufficient to set the pH of the composition to around 12.

Further provided by the invention is apparatus for inactivating a TSE agent comprising:
 a. a chamber for receiving contaminated material;
 b. means for controlling the temperature of the chamber; and
 c. a thermostable proteolytic enzyme active at alkaline pH, located within the chamber, the chamber optionally containing a solution of the thermostable proteolytic enzyme at a temperature of 45° C. to 85° C.

Further aspects of the invention provide for uses of the aforementioned compositions for the inactivation of TSE agents.

An advantage of the invention is its use in degrading TSE and similar agents, and it has been found in operation of particular embodiments of the invention that TSE-contaminated material has been successfully decontaminated using a combination of elevated temperature of around 50° C. to 70° C. and alkaline pH of around 9 to 12, with a thermostable, alkophilic proteolytic enzyme. Whilst it is on occasion possible to achieve some decontamination by extremely high temperature alone, it is of significant benefit to be able to inactivate TSE whilst avoiding extreme conditions, such as extremes of temperature, which lead to damage to the equipment being decontaminated In a separate, though related, aspect of the present invention, the problem of detecting infective material is addressed. If it were possible to test an item of equipment for contamination either prior to or after carrying out a sterilisation process, then this would be of significant utility.

An anti-prion antibody, mAb 6H4 is available commercially from Prionics, Switzerland. This antibody can be used to detect prion protein, detected typically using a second antibody conjugated to a detectable marker, which second antibody binds to the first.

A difficulty that has been discovered by the present inventors is that binding of this antibody to equipment suspected of being contaminated with prion, or equipment that is suspected to be contaminated but which has been subjected to treatment intended to destroy the prion, does not correlate with infectivity. It has, for instance, been discovered by the inventors that prion-infected mouse brain homogenate, digested with protease, and run on SDS-PAGE, then probed with anti-prion antibody, shows a negative result, that is to say absence of antibody binding. This material nevertheless retains infectivity.

A further object of the invention is to provide methods and reagents for identifying infective prion material and for determining when infective material has been removed by treatment.

Accordingly, a further aspect of the invention provides a method of examining prion-infected or suspected prion-infected material and determining whether dimers of prion protein are present.

This aspect of the invention is based upon a correlation between presence of dimers of prion protein and presence of infectivity. As the prion protein can exist in a number of different glycosylation states, references to dimer is intended to include dimers of the protein whether one or other or both is in any of a number of different possible glycosylation states. Reference to dimer is also intended to include reference to dimers of fragments of prion protein, those fragment-containing dimers retaining infectivity. Proteolytic treatment of the prion can result in removal of part of the protein sequence, leaving behind a residue which in dimer form retains infectivity, and these fragment dimers as well as prion-prion fragment dimers and fragment heterodimers are included within the definition of dimer in the present aspect of the invention.

The method enables detection of presence of dimer and hence enables detection of presence of infective material in cases where previous tests, designed to identify whether the monomer is present, would have given a negative result whereas in fact infectivity remained in that particular sample being tested. Hence, one advantage of the method is that at least some of the previous false negative results are eliminated. Avoiding these false negatives is clearly of significant value in testing alleged contaminated material as well as in testing material after treatment intended to remove infectivity.

As set out in more detail in an example below, prion dimers can be detected by using an antibody that binds to a prion monomer, using a second antibody, which has been labelled, to bind to the anti-prion antibody, and determining whether a protein is identified having approximately twice the molecular weight of the expected molecular weight of the prion monomer. As mentioned, the prion can be glycosylated in a number of different positions, typically 0, 1 or 2 positions, so when Western blotting is used, a number of bands may be seen on the resultant blot, corresponding to protein molecules having different glycosylation patterns. A known monomer is expected to have a molecular weight of about 33-35 kDa at its full length, however, it is routinely observed on SDS-PAGE gels and immunoblots as a limited proteolytic cleavage product known as “PrP 27-30”. Correspondingly, the dimer is expected to be found at that part of the blot corresponding to about 54-70 kDa.

The dimer forms may be probed using an antibody specific to the dimer, that is to say an antibody which binds to the dimer but substantially does not bind to the monomer form of the prion. This antibody may itself be labelled or may be probed using a secondary labelled antibody.

A preferred method of this aspect of the invention thus comprises a method of detecting prion infectivity comprising detecting prion dimer in a sample.

The invention additionally provides reagent for detecting prion dimers, and thus a further embodiment of the invention lies in an antibody specific for prion dimer, which antibody binds prion dimer but substantially does not bind prion monomer. This antibody optionally is labelled, and in an example described below the label is horseradish peroxidase; other suitable labels are alkaline phosphatase, beta galactosidase and D-biotin, though any suitable label may be used.

An alternative reagent for detection of presence of dimer comprises an antibody that binds to both monomer and a dimer and a molecular weight standard, such as one that corresponds to the molecular weight of the dimer. These are suitably used in combination with, for example, Western blotting techniques, to identify a protein having a molecular weight approximately twice that of the prion monomer. All these reagents are suitably incorporated into prion dimer detection kits.

To make an antibody selective for prion dimer, an animal is immunised with prion dimer and then serum extracted from the animal is run on a prion dimer column to identify antibodies that bind the dimer. These are then tested for cross-reactivity with prion monomer, with cross-reacting antibodies removed. The removal can be effected using a column loaded with prion monomer, the antibodies that emerge therefrom then being tested for absence of cross-reactivity.

Isolated prion dimer forms a further embodiment of the invention. This isolated material can be obtained simply by cutting out a portion of the SDS-PAGE gel used to resolve prion dimers. Alternatively, other separation techniques can be used to extract the prion dimer from homogenised prion-infected mouse brain. Antibodies that bind to the prion monomer and which are cross reactive can be used to confirm that the material thus obtained is prion dimer and not other protein of the same molecular weight.

As set out in more detail in the examples, prion strain 301V, a mouse passaged isolate, derived from a Holstein-Fresian cow terminally ill with BSE is used as an example of a prion strain. Infection is known to be produced by intracerebral inoculation and the incubation period required for the onset of clinical symptoms is remarkably uniform. That is to say, providing that the dose of infectious agent is sufficient then the classic signs of disease will appear at a defined time post-inoculation (in VM mice this is 120 days). For obvious reasons no-one has tested these properties on humans, however, the mouse bioassay is regarded as the closest available model and therefore a good indicator of BSE infection in man.

Using the Western blot detection system, in an example below, the monomer is apparently completely removed by protease digestion. Under these conditions, however, samples which were subsequently used in vivo did not prevent infection and may even have enhanced its onset. There must, therefore, be another source of infection other than the monomer. Since the monomer can be removed (or at worst dramatically reduced in concentration) this indicates a primary role in infectivity for the dimer—either alone or in combination with the monomer.

The second aspect of the invention thus also provides dimer removal using protease degradation according to the first aspect which is optionally enhanced by environmental conditions—high temperature, extremes of pH, and/or the use of detergents (e.g. SDS). As well as using single enzyme treatments, combinations of proteases and/or other enzymes can be used. For example, better degradation of the infective agent may be achieved by the addition of lipases, peptidases, glycosylases, nucleases and other enzymes.

To confirm dimer removal, a dimer cross-reactive antibody can be used in conjunction with a suitable detection system, one example being a sensitive in vitro detection system currently available from Invitrogen, referred to as Western Breeze, to confirm removal prior to further mouse bioassays.

BRIEF DESCRIPTIONS OF THE DRAWINGS

The methods and compositions of specific embodiments of the inventions are described in more detail below and are illustrated by the accompanying drawings and tables in which.

Figure 13:
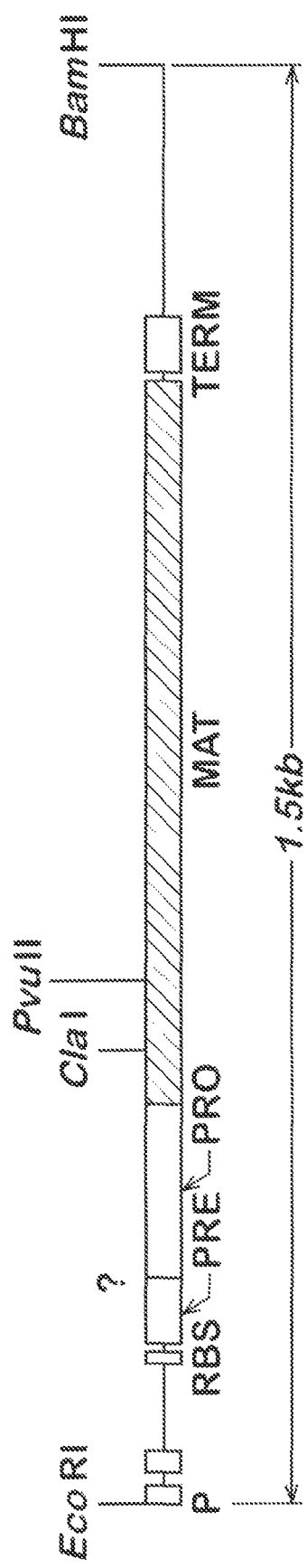

FIGS. 13.A, 13.B1, 13.B2 and 13.B3 depict the DNA (SEQ.ID.NO:1) and amino acid sequence (SEQ.ID.NO:2) for *Bacillus amyloliquefaciens* subtilisin and a partial restriction map of this gene.

FIG. 14 depicts the conserved amino acid residues among subtilisins from *Bacillus amyloliquefaciens* (BPN)' and *Bacillus lentus* (wild-type).

Figure 15:
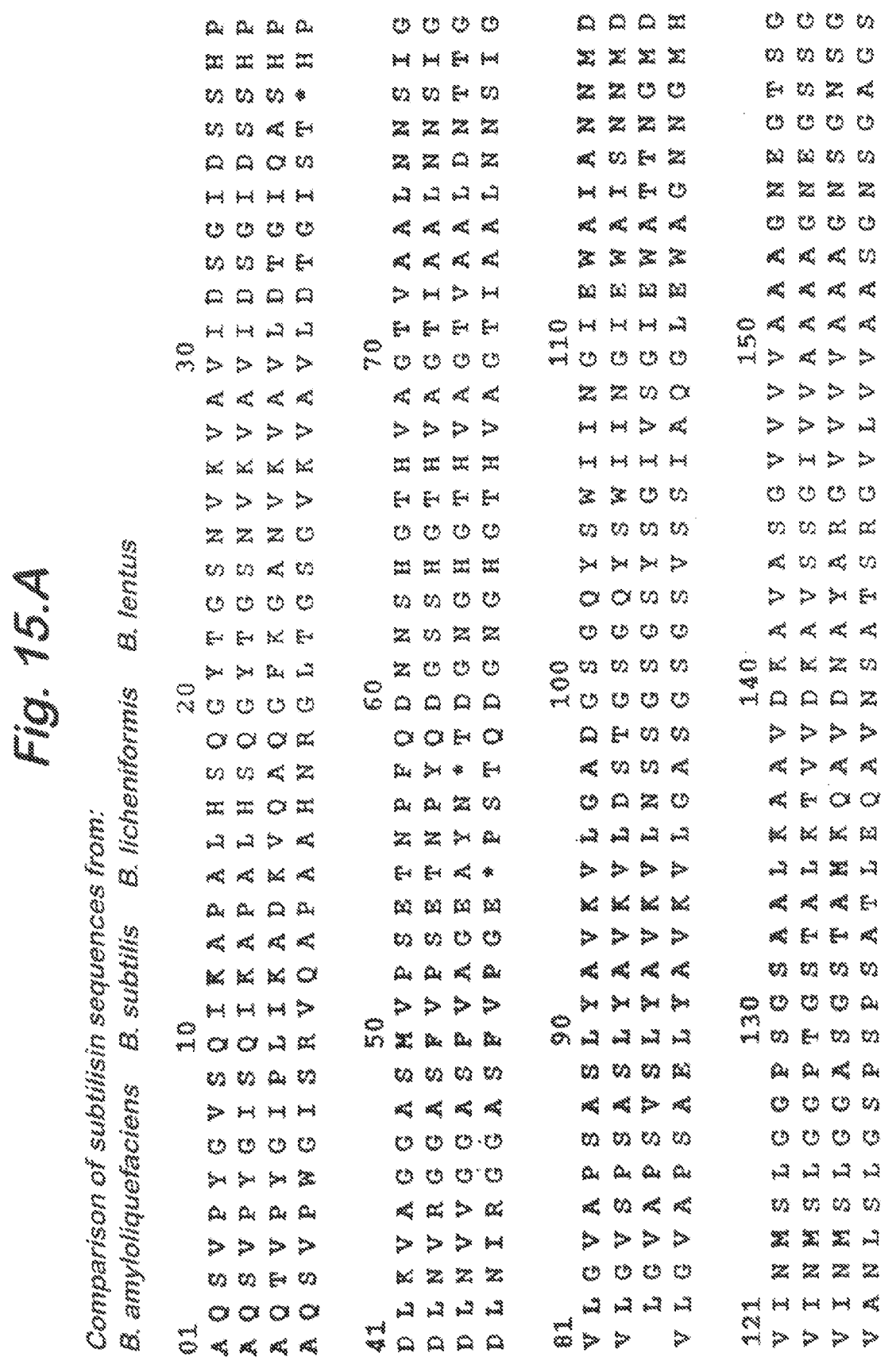
Figure 15:
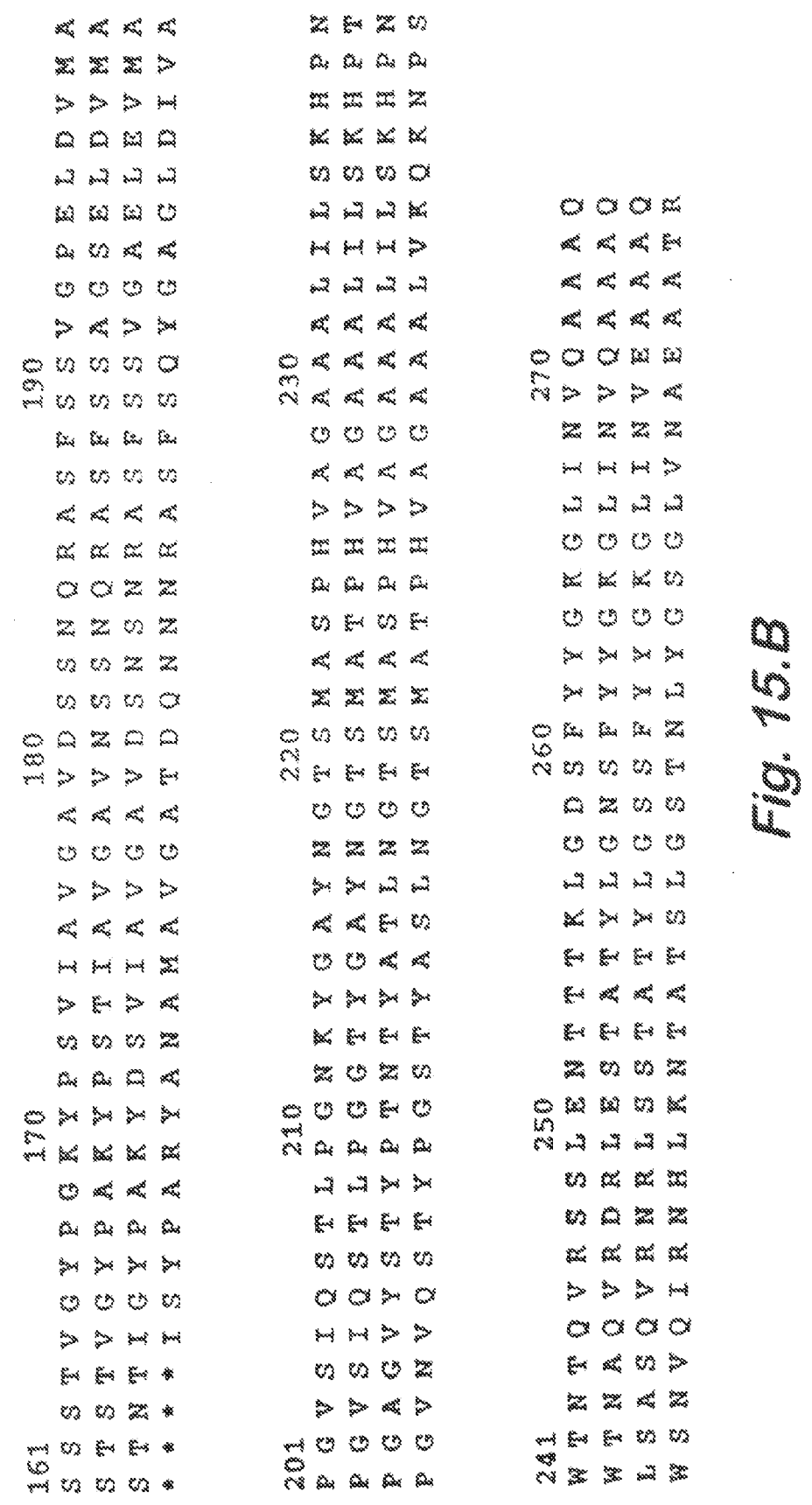

FIGS. 15A and 15B depict the amino acid sequence of four subtilisins. The top line represents the amino acid sequence of subtilisin from *Bacillus amyloliquefaciens* subtilisin (also sometimes referred to as subtilisin BPN') (SEQ.ID.NO: 7). The second line depicts the amino acid sequence of subtilisin from *Bacillus subtilis* (SEQ.ID.NO: 8). The third line depicts the amino acid sequence of subtilisin from *B. licheniformis* (SEQ.ID.NO: 9). The fourth line depicts the amino acid sequence of subtilisin from *Bacillus lentus* (SEQ.ID.NO:10). The symbol * denotes the absence of specific amino acid residues as compared to subtilisin BPN'.

Figure 16:
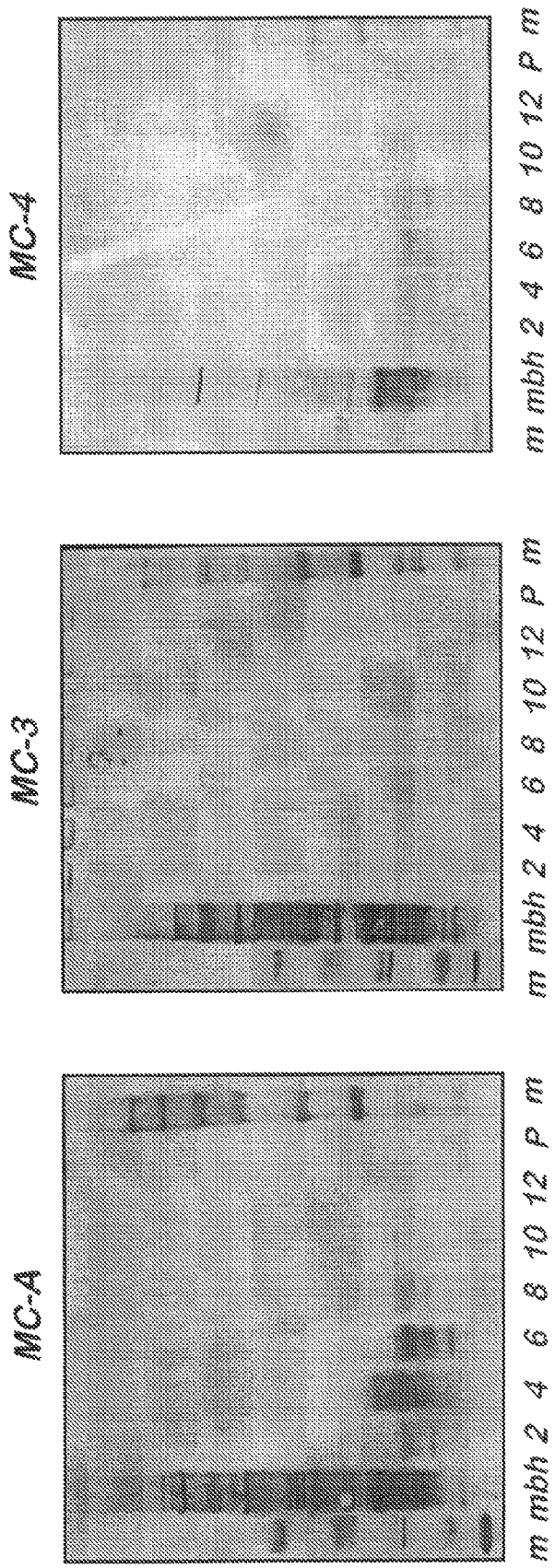

FIG. 16 shows an MC-A, MC-3 and MC-4 digest of mbh.

FIG. 17 shows a comparison of MC-A, MC-3 and MC-4 mbh digests with a Properase mbh digest.

FIG. 18 also shows a comparison of MCA, MC-3 and MC-4 mbh digests with a Properase mbh digest.

FIG. 19 shows a temperature profile of MC-3.

Figure 20:
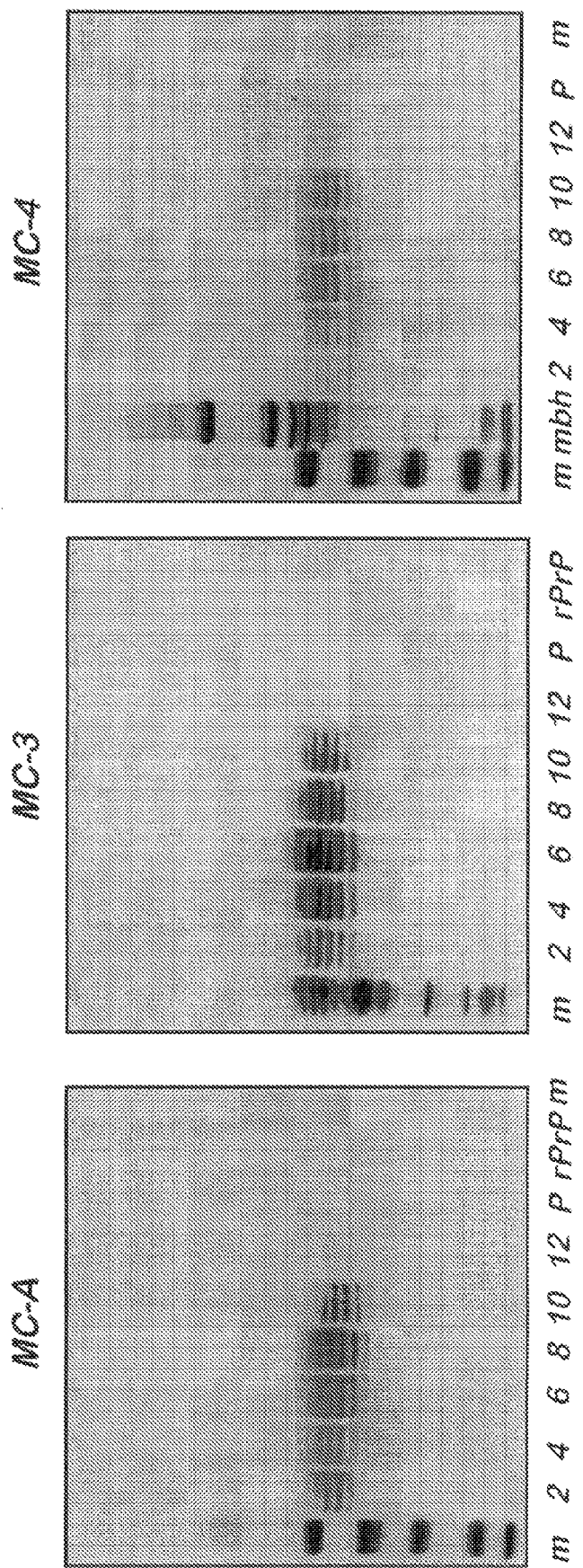

FIG. 20 shows detection of MC-A, MC-3 and MC-4 mbh digests with PAb2.

FIG. 21 shows MC-3 dilutions at pH 10 and pH 12.

Figure 22:
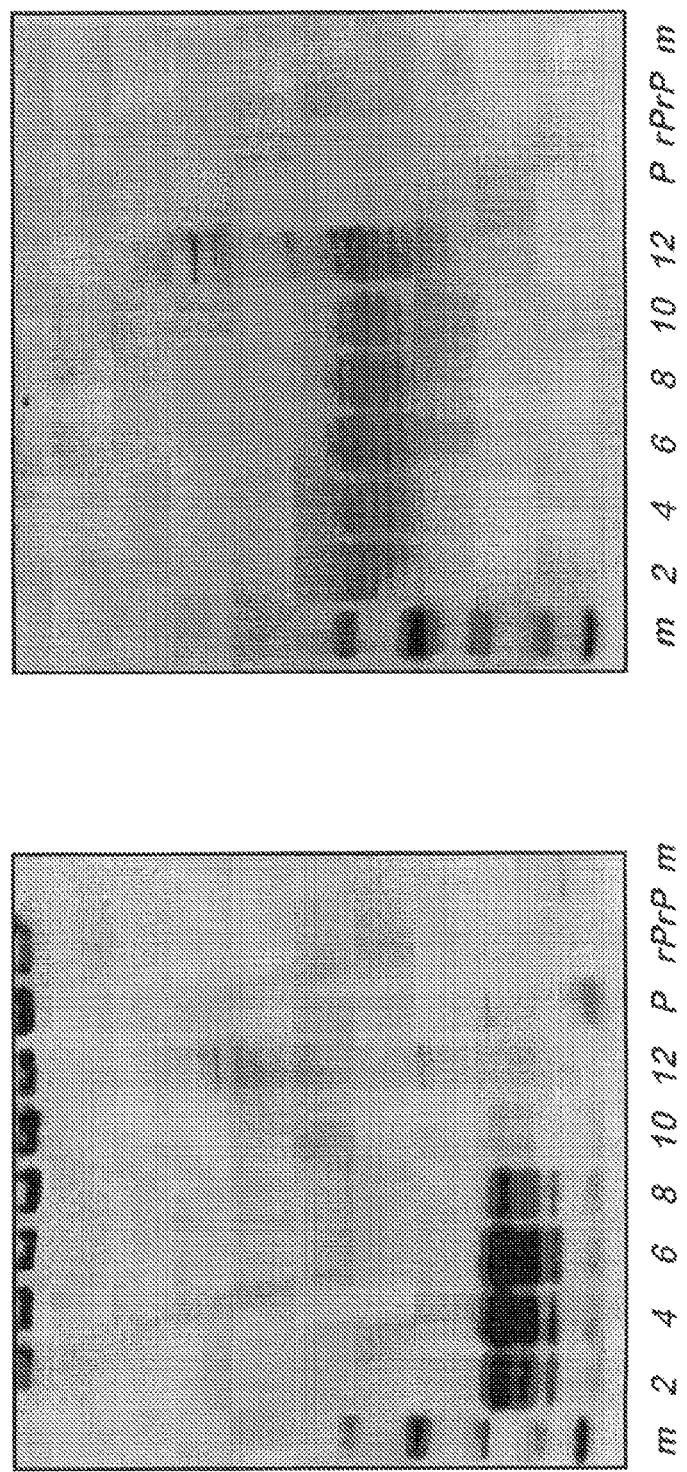

FIG. 22 shows a comparison of MC-A, MC-3 and MC-4 mbh digests with a Proteinase K mbh digest, Table 1 shows the incubation period of VM mice infected with BSE (301V)-infected mbh, Table 2 shows the incubation period of VM mice infected with BSE (301V)-infected mbh spiked into a background of meat and bonemeal (mbm).

Table 3 shows organisms from which thermostable proteases were analysed.

EXAMPLES

Example 1

VM Mouse Colony and Incubation with BSE (301V) Agent

Studies on the inactivation of the TSE agent, BSE strain (301V), required the establishment of a mouse breeding colony for the generation of both uninfectious and infectious brain homogenate (mbh) and its subsequent titration and bioassay. The VM mouse strain selected for use in the study was obtained from Dr David Taylor (Institute of Animal Health, Edinburgh). Six pairs were introduced into a dedicated room within an animal facility. Mice were screened for their health status and a breeding programme initiated.

BSE (301V) infectious mouse brain (IAH, Edinburgh) was prepared for inoculation by crude homogenisation followed by passage of the brains through increasingly fine gauge luer-locked needles (from 21 G-27 G) to and from a contained safety syringe into a closed septum-topped vial. This procedure was carried out in a validated safety cabinet within a containment level 3 (CL3) laboratory immediately prior to intracerebral inoculation of the VM mice. The anaesthetised (alphadolone/alphaxalone) mice were inoculated intracerebrally via 26 gauge needles with 20 microlitres of the mouse brain homogenate preparation. Forty-nine out of fifty mice survived this procedure. These were retained to allow incubation of the agent and the generation of the required quantity of high-titre infectious material.

Biomass Production

A wide variety of organisms were chosen for the production of biomass in order to provide as broad a selection of thermostable proteolytic enzymes as possible. Organisms selected ranged from those growing optimally at moderately thermophilic temperatures (50° C.) through to extremely thermophilic temperatures (100° C.) and included members of both the Archaea and the Bacteria. Thermophiles were also selected to cover a wide range of growth pH, encompassing pH optima from pH2.5 to pH11.5. The majority of organisms were grown in batch culture, however, where the growth requirements of the organism were particularly fastidious, continuous culture was used (Raven and Sharp (1997) Applied Microbial Physiology: A Practical Approach, Ch. 2, Eds. Stanbury and Rhodes, OUP pp. 23-52). Depending on the biomass yield of the organism being grown, batch culture volumes of between 20 L and 120 L were employed to achieve the desired amount of cell paste. The continuous culture system utilised either a 2 L or 5 L working volume gas lift bioreactor constructed entirely of glass and PTFE. More prolific organisms such as *Bacillus* spp., and *Thermus* spp., were pre-screened to select those with high levels of protease activity prior to their culture on a larger scale. A quick and sensitive fluorometric protease assay utilising microtitre plates was adopted for this purpose to permit high throughput screening (EnzChek™, Molecular Probes, Leiden, Netherlands).

Culture biomass was harvested by continuous centrifugation (Contifuge Stratos™, Kendro Laboratory Products, Bishop Stortford, UK) and stored at −80° C. Culture supernatants were concentrated with a 10 KDa cut off tangential flow filter (Pall filtration, Portsmouth, UK). Proteins were precipitated with ammonium sulphate (90% saturation) and stored at −80° C.

Protein Purification

A rapid protease screening and purification technique was required in order to process all of the crude protein preparations after the biomass production stage. A dye-ligand affinity chromatography system was used for this purpose (PIKSI M™, Affinity Chromatography Ltd., Isle of Man, UK). Initially, each crude ammonium sulphate precipitate was dissolved in buffer and passed through a desalting column. Each sample was then loaded onto the PIKSI M test kit, which contained 10 different affinity ligands. Fractions were then assayed for protease activity to determine the most suitable matrix for purification of the protease, either by positive binding of the target molecule and then elution, or by negative binding of contaminants. The purification was then scaled up using the same affinity matrix in conjunction with an FPLC system (Amersham-Pharmacia Biotech, Amersham, UK). By combining this technique with the fluorometric protease assay, the rapid screening of many fractions could be undertaken.

The fluorometric protease assay utilises casein derivatives that are heavily labelled with green fluorescent BODIPY FL in which the conjugates' fluorescence is almost totally quenched. Protease catalysed hydrolysis releases the highly fluorescent label and the resultant fluorescence can be measured on a fluorometric microplate reader (Labsystems Fluoroscan II™). The increase in fluorescence is proportional to protease activity and was compared with that of a standard protease (Protease X, Sigma-Aldrich, Poole, UK).

Protease Characterisation

A range of thermostable proteases were analysed (see Table 3). Direct characterisation of activity was carried out using the closest non-infectious analogue to BSE (301V)-infectious mouse brain homogenate available as substrate, i.e. normal VM mouse brain homogenate. Initial digests of total uninfected mouse brain homogenate (mbh) were performed over thirty minutes at 60° C. and at pH7.0. The samples were then boiled under reducing conditions and analysed by SDS-PAGE on pre-cast NuPage 4-12% Bis-Tris gels (Novex™, San Diego, US). Gels were fixed using standard procedures and the proteins visualised using the Novex colloidal blue staining kit. The results showed both the levels of activity of the proteases against the mbh substrate under these conditions and also the level of purity of individual proteases. Protease concentrations used in the assays were based on total protein concentration, therefore, a wide range of activities was observed from limited to complete digestion.

Activity profiles showing the full effect of pH and temperature on mbh digestion were then produced for each enzyme. Several enzymes showed extensive activity over the complete range of conditions (pH 2-12 and 50-100° C.). In general, however, complete digestion of mbh was only achieved over a narrower range indicative of the enzymes' pH and temperature optima. FIGS. 1 and 2 show the activity profiles for a sample protease, *Bacillus* protease M. As can be seen the enzyme is moderately thermophilic and gives complete digestion at temperatures up to 70° C. Similarly the pH profile indicates a preference for neutral or alkaline conditions.

Protease Testing

Several enzymes did not give complete digestion of mbh even when incubation times were increased to 24 hours. This may have simply been due to low protease activity, however, several highly purified and concentrated enzymes still only produced partial digests. In these reactions little enzyme-substrate interaction appeared to be occurring. It was considered that this could be due to non-proteinaceous material, e.g. lipids, surrounding the substrate and preventing interaction, however, pre-treatment with lipases and other enzymes had no observable effect (data not shown). A second possibility considered was the effect of repulsive surface charges between proteases and the substrate. One enzyme in particular, purified from *Bacillus thermoproteolyticus* Rokko, consistently produced poor digestion of mbh even at high concentrations. This enzyme was known to remain active in the presence of high levels of detergents, therefore, digests were performed with the addition of SDS in an attempt to overcome this effect. FIGS. 3 and 4 show *B. thermoproteolyticus* Rokko digests of mbh in the absence and presence of SDS. FIG. 3 clearly indicates that under standard conditions there is little difference in digestion even as the protease concentration is increased to 20 $mg.ml^{-1}$. On addition of SDS (lanes 2-5), no protein bands, except the protease itself, are visible indicating a complete digest. Tested proteases could, therefore, be divided simply into three categories: (i) those able to give total mbh digestion in the absence of detergent, (ii) those able to give total mbh digestion in the presence of SDS and (iii) those unable to digest the substrate fully. Proteases in categories (i) and (ii) were selected for immediate further study, while those in category (iii) were either rejected or assumed to be required in greater quantity and/or higher purity.

Western Blotting of Mouse Brain Homogenate

Mbh proteins were transferred onto nitrocellulose and blocked overnight in PBS-Tween (PBST)+3% skimmed milk powder. The membrane was washed (×3 in PBST) and incubated for 1 hour with 6H4 anti-human recombinant PrP monoclonal antibody (Prionics, Zurich, Switzerland). After a second washing step, anti-mouse HRP-conjugate was added and the membrane incubated for 1 hour. Washing was repeated and the antibody reaction visualised by addition of TMB (Harlow and Lane (1988), Antibodies: A Laboratory Manual, Cold Spring Harbor Press).

FIGS. 5 and 6 show an SDS-PAGE and an immunoblot of undigested mbh respectively. Although there is some non-specific background, dark bands indicating the presence of mouse prion can clearly be seen at the expected molecular weight (~33-35 kDa). Distinct bands are also visible at ~66-70 kDa, which may correspond to prion dimers previously reported (Safar et al. (1990) Proc. Natl. Acad. Sci. USA, 87: pp 6373-6377).

Western transfer and immunoblotting were used to confirm that no immunoreactive fragment of mouse $PrP^c$ remained after digestion. FIG. 7 shows mbh digested to completion with three closely related thermostable proteolytic enzymes (Proteases G, R and C), as assessed by SDS-PAGE. In the corresponding immunoblot (FIG. 8) only 2 bands are visible, both with an apparent MW of ~23 kDa. The strong band in lane 9 corresponds to recombinant mouse PrP (+ve control), whilst the weak band in lane 4 appears to be due to a slight reaction with the heavily loaded enzyme preparation. In this case, complete loss of $PrP^c$ immunoreactivity is still apparent since no band is observable in lane 3.

Preparation and Titration of Infectious Mouse Brain Homogenate

Eighty days post challenge onward, mice were subject to daily clinical scoring to detect clinically affected mice as early as possible. A single mouse died of an unknown cause prior to this period. The remainder exhibited the expected disease progression and were sacrificed between 110 and 130 days post challenge. The brains were removed aseptically and stored frozen until required. Forty-eight BSE (301V) infectious VM mouse brains were homogenised in four volumes of PBS within a contained homogeniser then passed sequentially through increasingly fine gauge needles (21 G to 26 G) until free flowing. A sample with a further 2-fold dilution (1:9 mouse brain: PBS) was prepared for titration of infectivity. Over 800×0.1 ml aliquots of BSE (301V) infectious mouse brain homogenate were prepared. These procedures were again carried out under rigorous class III containment, including the wearing of positive pressure respirators.

Groups of 25 eight week old VM mice received titration doses of the infectious mouse brain homogenate preparation at 10 fold dilutions from $10^{-1}$-$10^{-8}$. A further group of 25 mice were challenged with uninfectious mouse brain homogenate as a control. All mice were inoculated under anaesthetic using 26 G×⅜" (0.95 cm) needles with plastic sleeve guards cut off 2 mm below bevel in a Class 2 cabinet with the use of an injection guard. The mice were then left to incubate the BSE (301V) agent for extended periods some in excess of a year. The initial titre of the infectious mouse brain homogenate preparation was established retrospectively once all incubations (clinical monitoring at 80 days onwards) were complete.

Dimer Detection in Digested Mouse Brain

BSE (301V)-infected mouse brain homogenate was digested at neutral pH and 60° C. for 30 minutes with protease. Total protein digests were run on SDS-PAGE and transferred by Western blotting to nitro-cellulose membranes. These were cut into strips and probed with CAMR anti-prion antibodies (produced in rabbits). A second generic antibody (goat anti-rabbit) was conjugated to horseradish peroxidase and used with detection by TMB colorimetric substrate.

At the time, the expected result was that the results were the same as the control blot (number 7).—using the anti-prion antibody mAb 6H4 (from Prionics, Switzerland). In this control blot, there is seen the typical three-banded pattern (glycosylation states) for protease-digested infectious-conformation prion protein (PrP$^{Sc}$).

However, the blots in this example did not show this pattern. Blot 1 uses a polyclonal antibody raised against a PPD-conjugated peptide corresponding to an N-terminal region of the prion molecule. Nothing is seen in the lanes. This section of the protein is susceptible to proteolysis, so it is not surprising to see nothing in the lanes (2 & 3)—see FIG. 9, blot 1 on left hand side. Lane 1 is a molecular weight marker.

Blot 2 has a second antibody raised against a peptide sequence further into the prion molecule. This shows at least 9 bands of varying intensity, approximately equidistant, at a molecular weight corresponding to a prion dimer with a range of glycosylation states—see blot 2 on FIG. 9.

Figure 1:
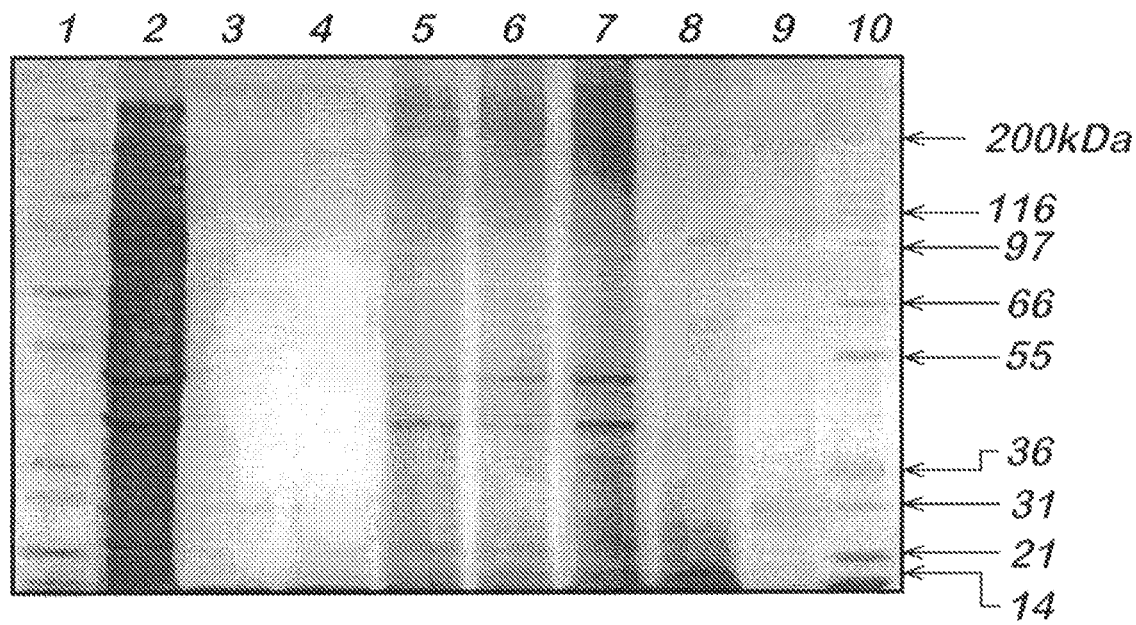
FIG. 1 shows the effect of temperature on a protease M digest of mouse brain homogenate (mbh)
Figure 2:
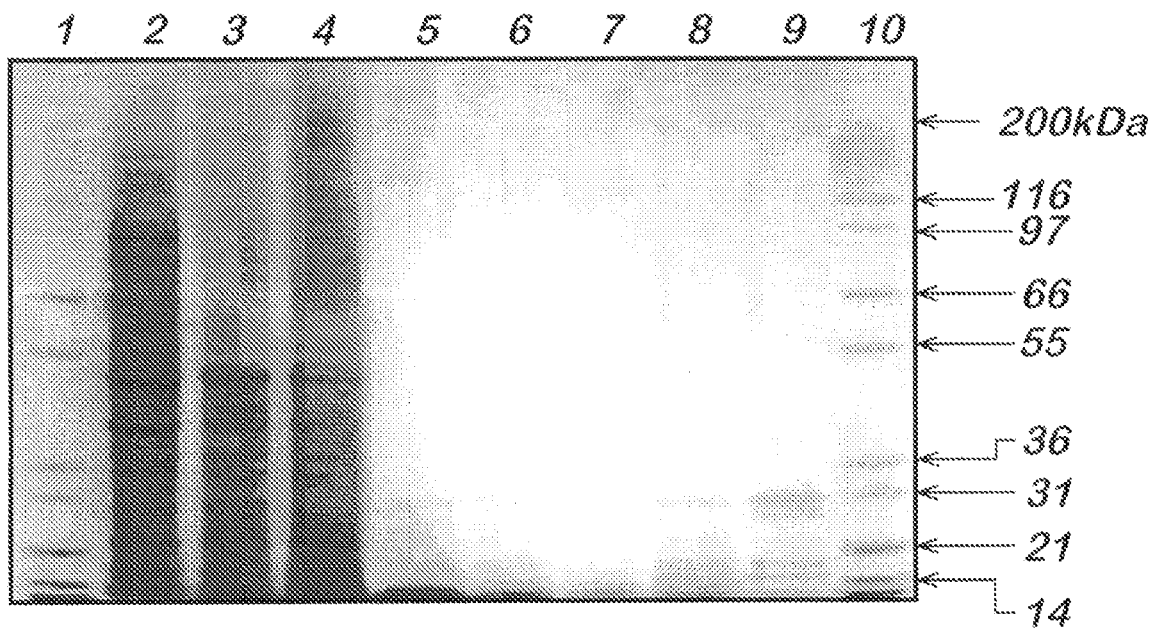
FIG. 2 shows the effect of pH on a protease M digest of mbh.
Figure 3:
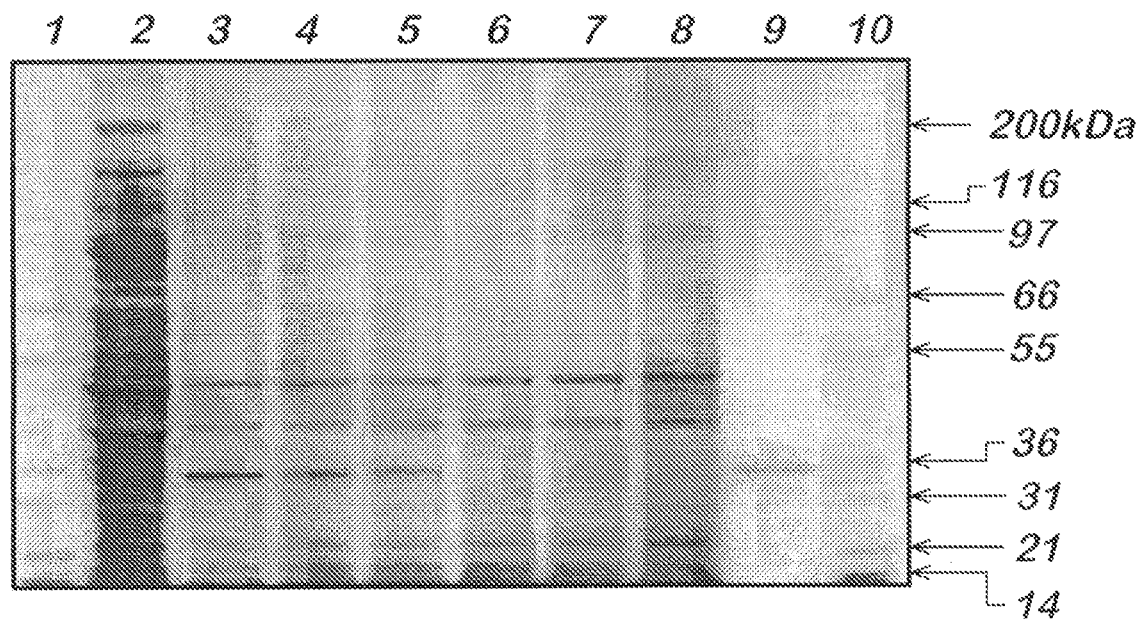
FIG. 3 shows a *Bacillus thermoproteolyticus* Rokko digest of mbh.
Figure 4:
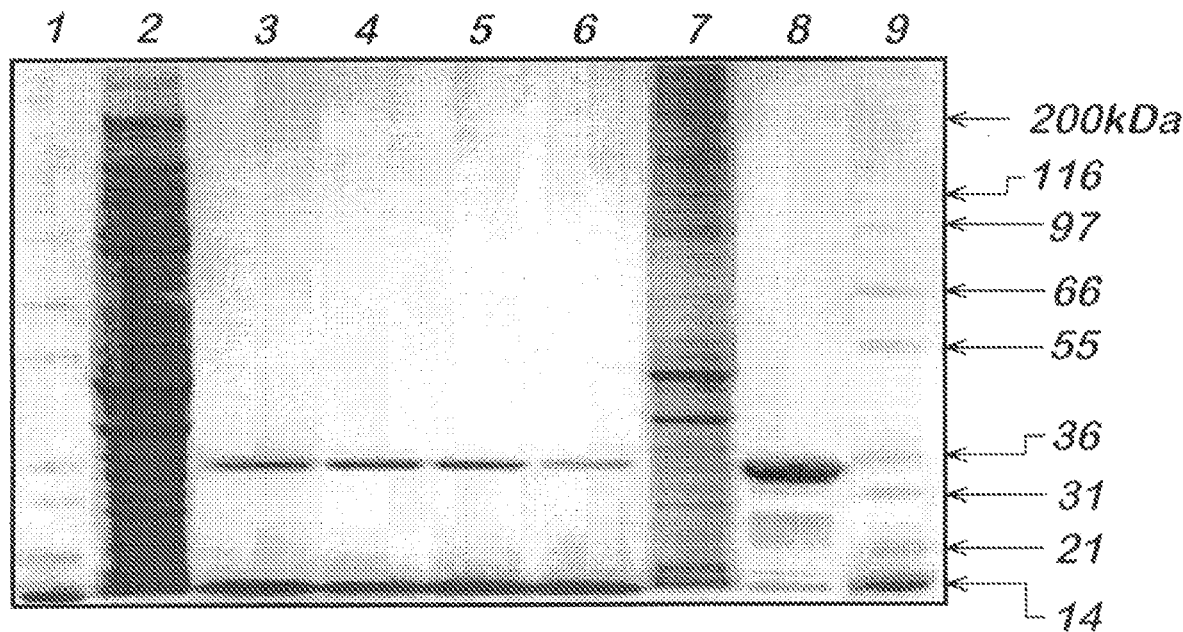
FIG. 4 shows the effect of sodium dodecyl sulfate (SDS) on a Rokko digest of mbh.
Figure 5:
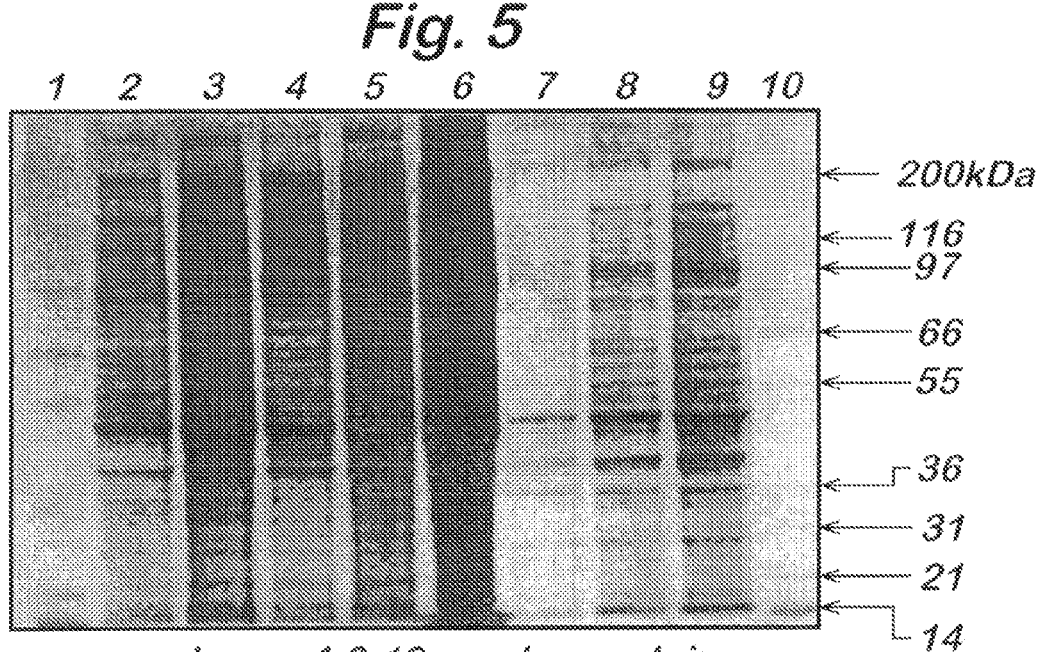
FIG. 5 shows and SDS-PAGE of mbh.
Figure 6:
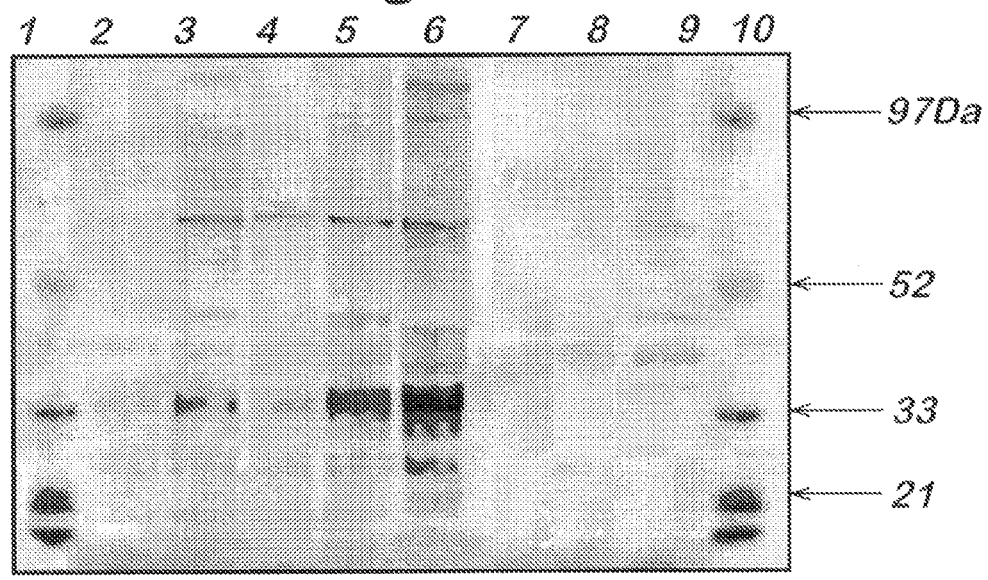
FIG. 6 shows and immunoblot of mbh.
Figure 7:
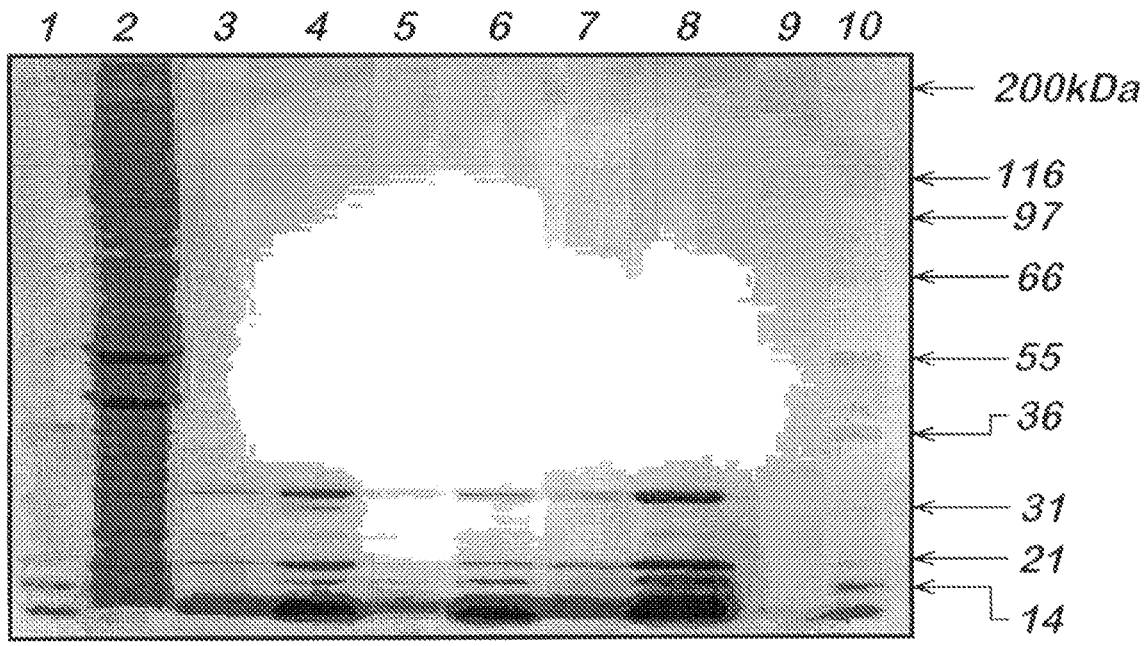
FIG. 7 shows a protease G, R and C digest of mbh.
Figure 8:
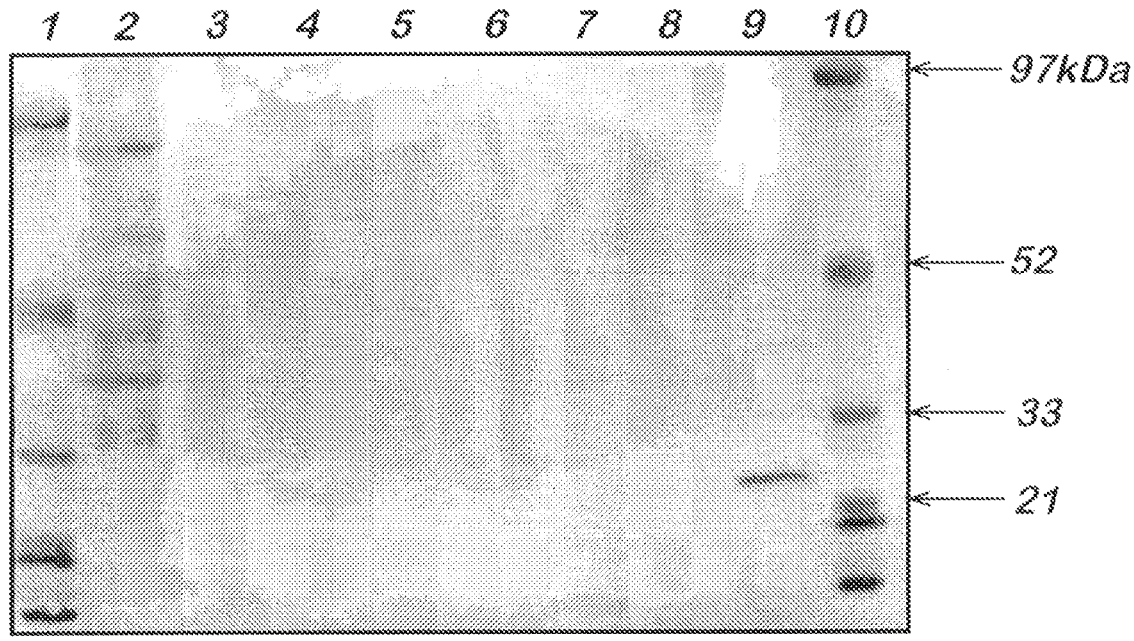
FIG. 8 shows an immunoblot of the digest in FIG. 7.
Figure 9:
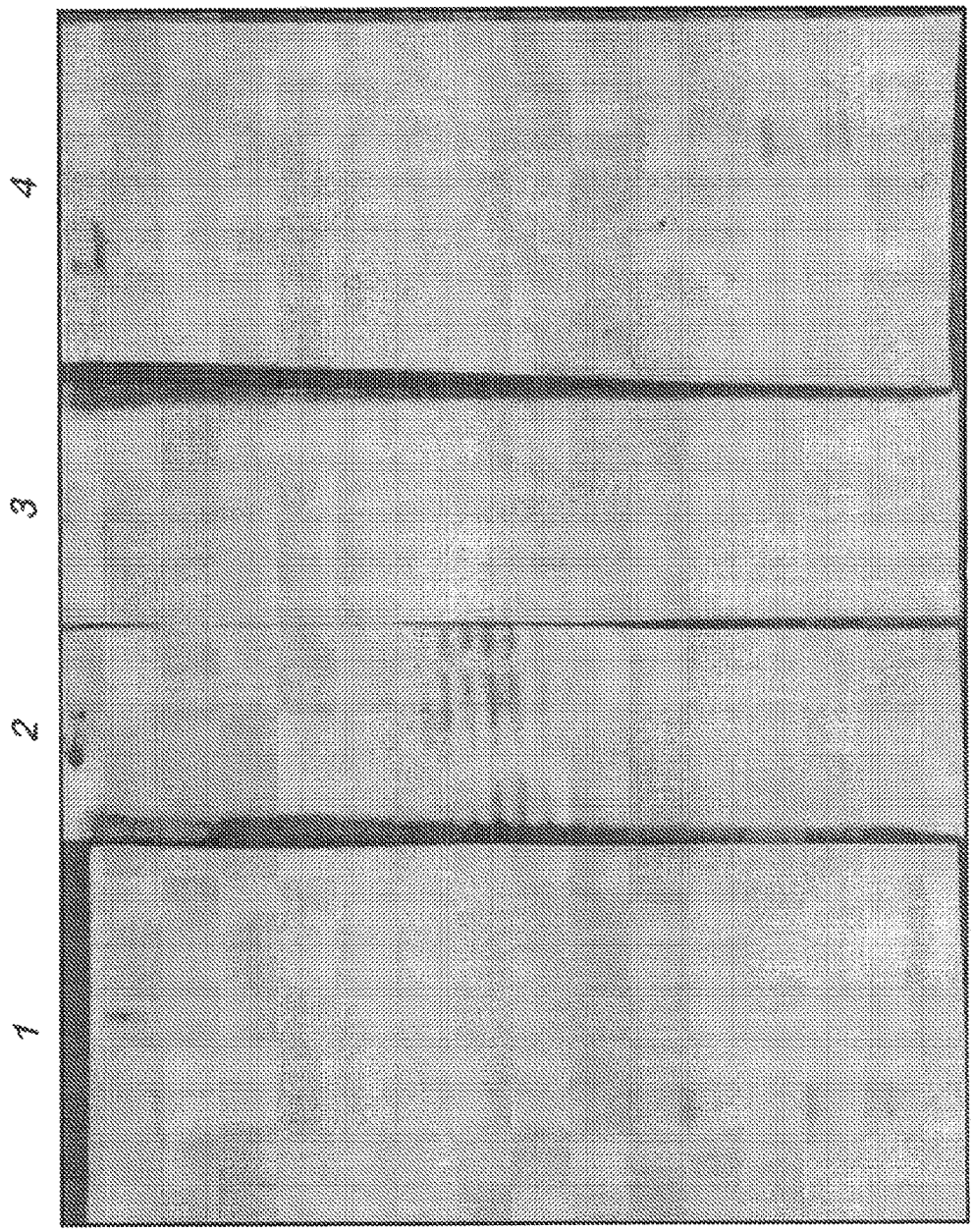
FIGS. 9 to 12 show blots of BSE (301V)-infected mouse brain homogenate, to illustrate correlation of infectivity with prion dimer, and as further explained in the examples below.

Blot 3 antibody shows similar profile; blot 4 is also shown but its results are too poor quality to draw any conclusions—see blots 3 and 4 on FIG. 9.

Figure 10:
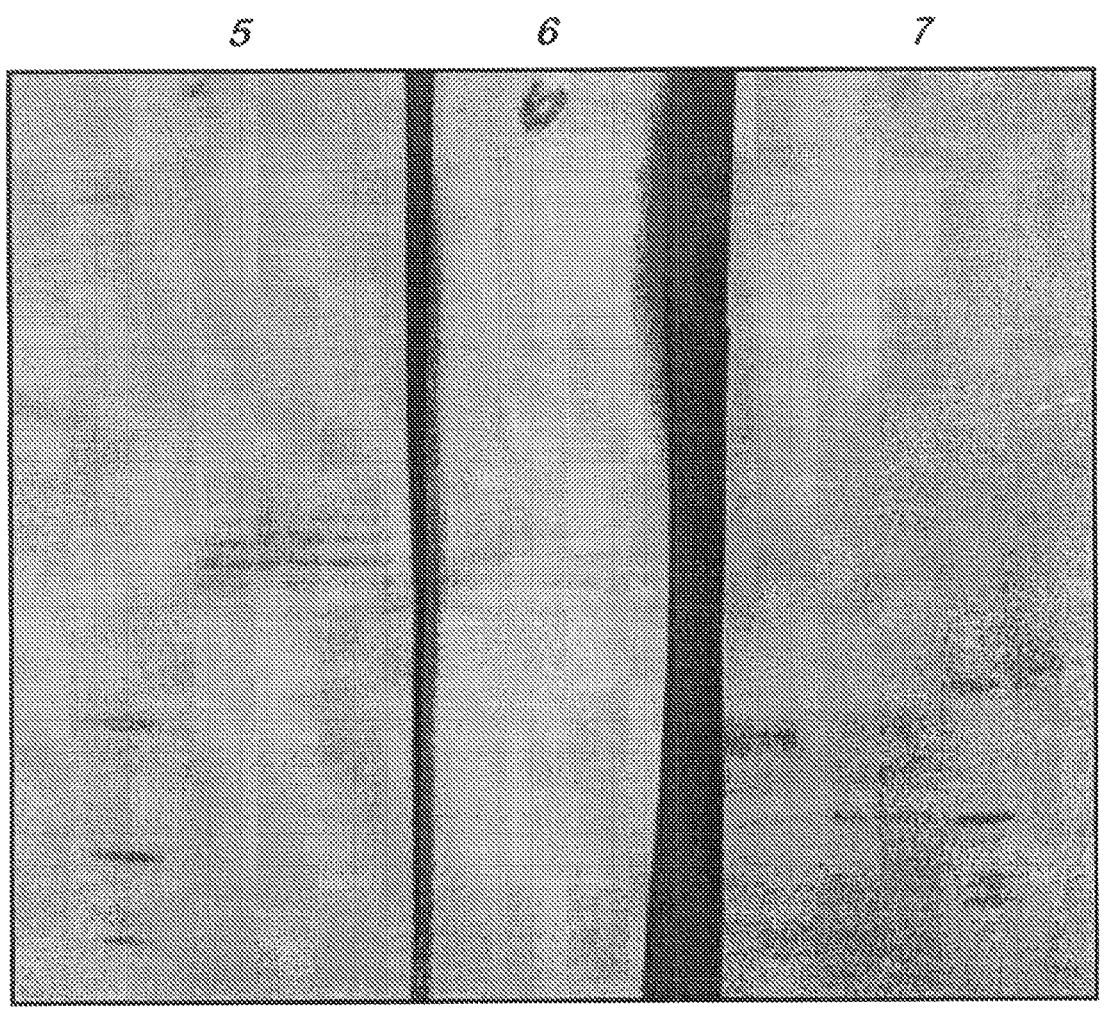
Figure 11:
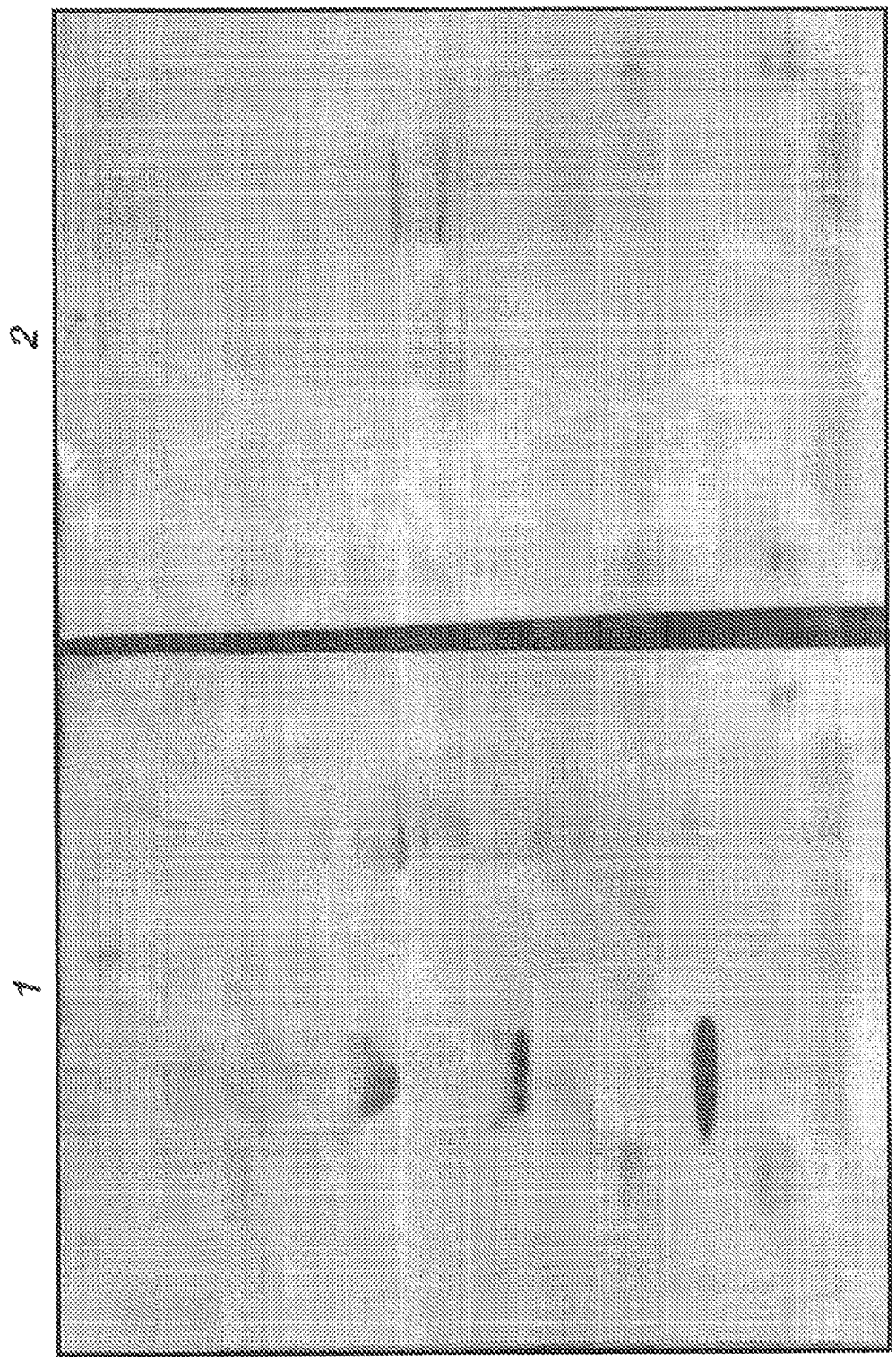
Figure 12:
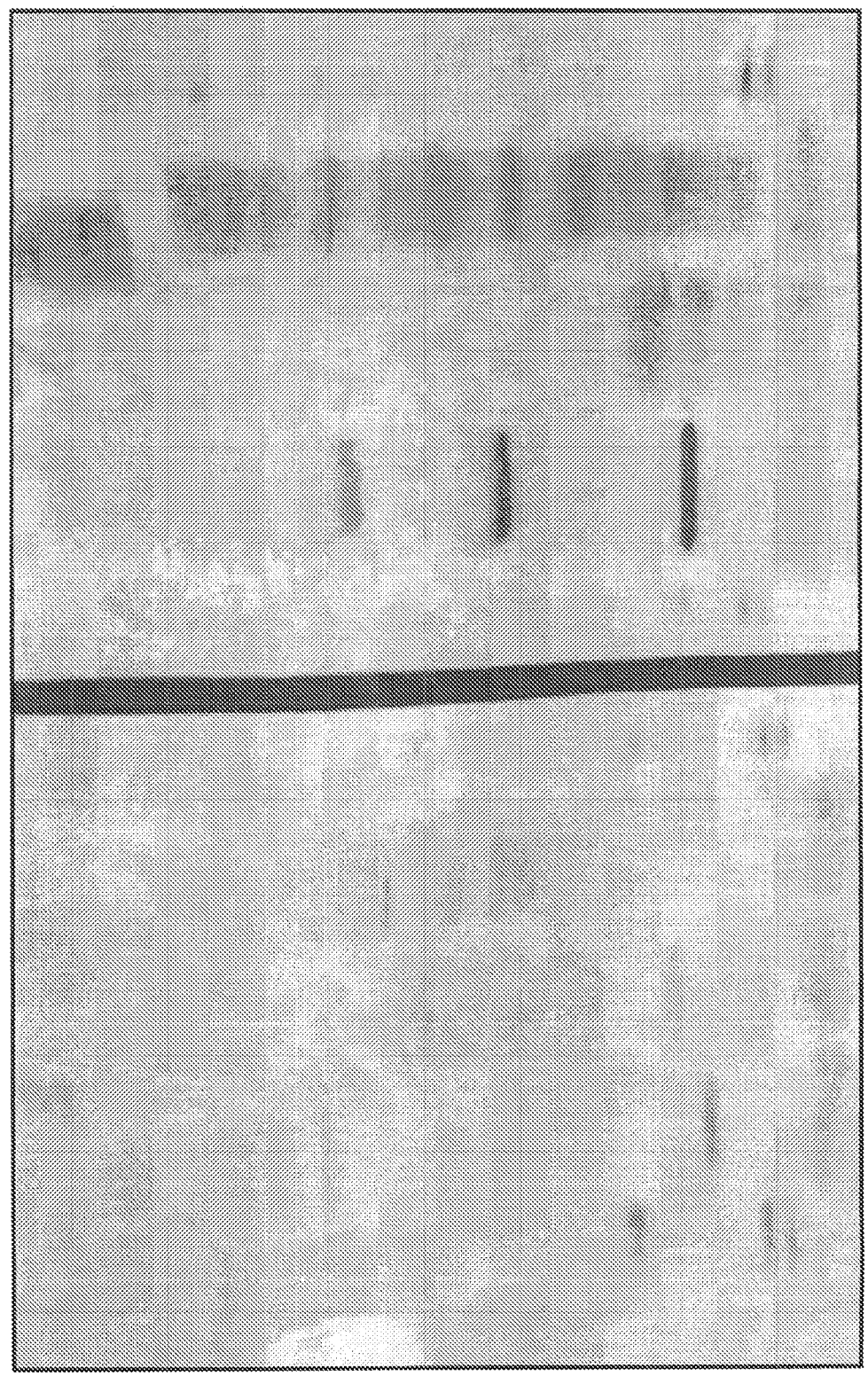

Blots 5 and 6, shown on FIG. 10 with the control blot 7, again show the multi-banded pattern Dimer Detection in Digested Mouse Brain The above example was repeated, and the results shown in FIGS. 11 and 12.

Blot 1 shows molecular weight markers in lanes 1 and 5. Lane 2 is recombinant murine PrP showing recombinant murine PrP oligomers. Lane 3 shows lack of antibody response to protease-digested infectious mouse brain homogenate. Lane 4 is the antibody response in the undigested control.

Blot 2 is as above but shows the previous banding pattern in the protease digested sample.

Blot 3 shows the antibody 3 response. Here there is some response to recombinant murine PrP (lane 2). Lane 3 shows not only the multiple (dimeric PrP) banding pattern, but also some monomeric PrP response.

Blot 7 is the 6H4 mAb antibody control. Here there is good detection of recombinant murine PrP oligomers (lane 2).

Lane 3 shows the heavily diglycosylated form of limitedly protease-treated PrP$^{Sc}$, plus the more minor monoglycosylated and non-glycosylated forms typical of BSE (301V) strain. No 'dimer' detection is apparent.

Preparation of Antibodies Including Dimer Preferential Antibody

In the examples, we have used 6 polyclonal antibodies Of these, three detect the dimer alone and do not bind the monomer whereas one cross-reacts with both the monomer and the dimer.

The polyclonal sera were produced by immunisation of rabbits with synthesised prion mimetic peptides. These peptides were designed based on regions of high homology between human, mouse and bovine prion protein amino acid sequences.

The sequences producing the dimer-reactive antibodies were as follows:

```
CGGWGQPHGGC                   (Peptide 2)

CGGYMLGSAMSRPIIHFGNDYEC       (Peptide 3)

CVNITIKQHTVTTTTKGENFTETDC     (Peptide 5)

CITQYQRESQAYYQRGASC           (Peptide 6)
```

The peptides were synthesised with a cysteine at both ends (see above) and with a cysteine at one end only. This method was used in order to present both the linear form and a loop structure of the antigen on the surface of the carrier protein.

The peptides were synthesised commercially and coupled to the carrier protein PPD (purified protein derivative), derived from an attenuated strain of the bacterium *Mycobacterium bovis*, which is lyophilised and used to conjugate to the peptide via a linker.

Anti-prion polyclonal antibodies were produced as follows:

A sample of pre-immune sera (~1 ml) was collected from each of a group of Dutch rabbits.

The rabbits were injected with reconstituted freeze-dried *Bacillus* Calmette-Guerin (BCG) vaccine for intradermal use. A dose of 0.1 ml of reconstituted BCG vaccine was given in two sites in the scruff of the neck of the rabbit.

After 4 weeks, 0.6 mg of each peptide-PPD conjugate was measured (0.3 mg of each of the 1 cysteine and 2 cysteine versions) and dissolved in 1 ml of sterile 0.9% saline.

An equal volume of incomplete Freunds adjuvant was added and 0.75 ml aliquots, of the resulting emulsion, were injected intra-muscularly into each hind limb and 0.25 ml aliquots into two sites in the scruff of the neck per rabbit.

After 4 weeks a boost injection was given comprising of the peptide-PPD conjugates prepared as in step 3 and 4. The boost injections consist of four 0.25 ml injections into the scruff of the neck of each rabbit.

7-14 days after the first boost injections, 4 ml test bleeds were taken, the sera was assessed by ELISA for antibody titre.

A second boost injection was given 4-6 weeks after the first.

A third boost injection given 4-6 weeks later.

A 4 ml test bleed was taken 6-8 weeks after the third boost injection and antibody titres determined by ELISA A fourth boost injection given.

A 4 ml test bleed was taken 7-14 days after the fourth boost injection and antibody titre determined by ELISA.

Terminal exsanguination was carried out and blood collected. The serum was separated by centrifugation and stored at −20° C.

Analysis of antibody titre was achieved using ELISA. The immunoassay plate was coated with the same peptides conjugated to a different carrier protein (KLH) in order to differentiate the response to the peptide from the response to the carrier protein.

Three of the antibodies produced by immunisation of the synthetic peptide sequences described bind preferentially to the dimer form of the molecule.

Analagous steps may also be used to prepare a monoclonal antibody. This could be achieved using a method such as described in Antibodies—A Laboratory Manual, Ed Harlow and David Lane, 1988 (Cold Spring Harbor Laboratory).

Example 2

Evaluation of Proteases MC-A, MC-3 and MC-4

Three new proteases, MC-A, MC-3 and MC-4, were assessed using infectious BSE (301V) mouse brain homogenate (mbh) dialysed to pH 2, 4, 6, 8, 10 and 12 respectively and digested at 50° C. for 30 minutes. Total protein digests were run on SDS-PAGE and transferred by Western blotting to nitro-cellulose membranes.

The Western blots were detected with 6H4 and TMB colorimetric substrate, and the results shown in FIG. 16.

FIG. 16 demonstrates characteristic $PrP^{Sc}$ monomer bands present after digestion with the new proteases at pH 2-10. The monomer bands present after digestion with MC-3 at pH 2-10 appear very faint. Indeed, of the three proteases tested, MC-3 shows the greater reduction of monomer.

In addition, no $PrP^{Sc}$ monomer bands are present at pH 12 with any of the three proteases.

Comparison of New Proteases with Properase

The digestion of $PrP^{Sc}$ monomers using the three new proteases was compared to digestion using Properase, and the results shown in FIGS. 17 and 18.

FIG. 17 demonstrates monomer digestion at pH 2-12 by MC-A, MC-3 and MC-4 at a temperature of 50° C., compared to Properase at 60° C. At 50° C., the three new proteases give improved monomer digestion compared to Properase at 60° C.

FIG. 18 shows monomer digestion at pH 2-12 by MC-A, MC-3 and MC-4 at a temperature of 60° C., compared to Properase at 60° C. At 60° C., digestion of the monomers with the three new proteases is comparable to that using Properase.

Temperature Profiling of MC-3

The effect of temperature on monomer digestion by MC-3 was investigated, with results shown in FIG. 19.

FIG. 19 shows increased temperature to result in increasingly incomplete digestion of mbh at low pH. However, at high pH (pH 10 and above), increased temperature leads to less distinct monomer bands. This suggests that at increased temperatures, high pH enhances digestion of monomer by MC-3. It is also noted that MC-3 at 50° C. has a greater effect across the pH range than either MC-A or MC-4.

Detection with PAb2

Mouse brain homogenates at pH 2-12 were digested at 50° C. for 30 minutes and the corresponding Western blots detected with a chemiluminescent detection substrate, PAb2. The results are shown in FIG. 20.

FIG. 20 shows high molecular weight (HMW) bands present after digestion with each protease at pH 2-10. The HMW bands at pH 12 are much reduced with all three proteases. This implies that the HMW bands are proteinaceous, as they can be removed by proteases. These bands are thought to represent $PrP^{Sc}$ dimers.

MC-3 Dilutions at pH 10 and pH 12

FIG. 21 shows the results of MC-3 dilutions at pH 10 and pH 12.

At pH 10, monomer bands are seen at 1:20 dilution and HMW bands are seen across the dilution range. However, at pH 12, no monomer bands are apparent and HMW bands are much reduced across the dilution range. This suggests high pH enables MC-3 to digest HMW dimer.

Comparison with Proteinase K

The ability of the three new proteases to digest monomer and HMW dimer was compared to Proteinase K, and the results shown in FIG. 22.

The results indicate that all three new proteases are better at removing both the monomer and the HMW dimer than Proteinase K.

Summary of Results

Of the proteases tested, MC-3 shows the greater reduction of the monomers.

MC-3 is better at removing the monomer bands across the pH range than either Properase or Proteinase K. Unlike Properase or Proteinase K, the new proteases reduce the HMW bands at pH 12.

Example 3

Protocol for Protease Digestion of Mouse Brain Homogenate (MBH)

BSE (301V) infectious VM mouse brain homogenate was digested with MC3, MC4, proteinase K, properase, Purafect or Purafect ox and used to infect VM mice as outlined below:

Preparation of Protease Treated Infectious MBH and Controls.

2×500 μl of infectious MBH was microdialysed against an excess of pH12 buffer (or as appropriate) for 30 minutes. The aliquots were combined and separated into 2 lots:

Lot 1: 100 μl of infectious MBH as positive control

Transfer 90 μl to fresh tube and add 10 ml of H2O

Heat at 50° C. for 30 minutes (or as appropriate)

Neutralise by addition of 11 μl of 10× phosphate buffer, pH7.0

Heat at 100° C. for 10 minutes

Dilute with 889 μl of PBS

Mix, take 100 μl aliquot and dilute in further 90 μl PBS (overall 1:100 dilution)

1 ml positive control ready for inoculation

Lot 2: 900 μl of infectious MBH for protease treatment

Divide into 10×90 μml aliquots

Add 10 μl of protease solution (neat) to each aliquot

Heat at 50° C. for 30 minutes (or as appropriate)

Neutralise by addition of 11 μl of 10× phosphate buffer, pH7.0

Heat at 100° C. for 10 minutes

Pool all aliquots and mix 1 ml of infectivity test material ready for inoculation Preparation of Controls to Assess Toxicity of Non-Infectious MBH in the Presence or Absence of Protease.

Additional controls to assess the toxicity of protease treated MBH (in the absence of infectivity) were prepared as described below:

Microdialyse 1×500 μl of uninfectious MBH against pH 12 buffer (or as appropriate)

Divide into 5×90 μl aliquots

Add 10 ml of protease solution (neat) to each aliquot
Heat at 50° C. for 30 minutes (or as appropriate)
Neutralise by addition of 11 µl of 10× phosphate buffer, pH7.0
Heat at 100° C. for 10 minutes
Pool all aliquots and mix
0.5 ml of toxicity test material ready for inoculation
Inoculation of VM Mice with Mouse Brain Homogenate.

VM mice were inoculated with 20 µl test material intracerebrally according to published methods. The test samples were MC3, MC4, proteinase K, properase, Purafect and Purafect ox digested infectious MBH, infectious MBH treated at pH 12 in the absence of protease, and toxicity controls of protease treated MBH (in the absence of infectivity) and the titration series.

Mice were scored on the basis of clinical symptoms and sacrificed at a defined clinical end-point. The results are shown below and expressed as the mean incubation period before sacrifice

TABLE 1 showing incubation period of VM mice infected with mouse brain homogenate (mbh) infected with BSE-301V. Infectious mbh was treated with MC3, MC4, proteinase K, properase, Purafect, or Purafect ox, treated at pH12 alone (positive control). For comparison incubation periods for a serail dilution of infectious mbh are shown. No toxic effects of MC3 or MC4 were observed in the absence of infectious material.

| Treatment | Number of mice | First death | Last death (number of survivors) | Mean assuming any remaining mice are all sacrificed on current day | SD | Number of healthy mice; no clinical symptoms |
|---|---|---|---|---|---|---|
| MBH study | | | | | | |
| MC3 | 18 | 173 | >277 (13) | 259.16 | 31.56 | 10 |
| MC4 | 20 | 143 | 147 | 145.96 | 1.41 | |
| Proteinase K | 22 | 187 | >282 (11) | 254.9 | 35.66 | 0 |
| Properase | 24 | 137 | 169 | 147.54 | 7.71 | |
| Purafect | 25 | 112 | 144 | 132.04 | 8.23 | |
| Purafect Ox | 24 | 125 | 146 | 132.83 | 4.76 | |
| Titration study; infectious MBH (iMBH) | | | | | | |
| Positive control 1:100 | 15 | 133 | 167 | 142.87 | 9.62 | |
| MBH × 1 | 10 | 112 | 142 | 120 | 8.5 | |
| MBH × $10^{-1}$ | 16 | 117 | 142 | 125.37 | 7.16 | |
| MBH × $10^{-2}$ | 23 | 124 | 143 | 135.78 | 5.59 | |
| MBH × $10^{-3}$ | 23 | 126 | 168 | 141.57 | 11.04 | |
| MBH × $10^{-4}$ | 25 | 137 | 198 | 157.52 | 18.5 | |
| MBH × $10^{-5}$ | 25 | 150 | 448 | 226.96 | 94.81 | |

The results indicate that *B. subtilis* enzyme properase and the *B. licheniformis* subtilisin MC4 reduce the levels of infectivity by greater than 3-logs (mean incubation times of 147.54 and 145.95 days compared to an incubation at $10^{-3}$ dilution of 141.57 days). MC3 and proteinase K both reduce the levels of infectivity by significantly more than 5 logs and exceed the lowest detection levels of the assay with a number of mice remaining alive after the incubation shown (277 and 282 days respectively). Of the 2 enzymes, treatment with MC3 shows the presence of >50% of mice with no clinical symptoms at 277 days whilst those surviving after treatment of infectious material with proteinase K all show some signs of clinical disease after 282 days. Treatment with either Purafect or Purafect Ox reduce the levels of infectivity by nearly 2 logs whilst pH treatment alone results in a 1 log reduction in infectivity.

Example 4

Protocol for Protease Digestion of Meat and Bone Meal (MBM)

BSE (301V) infectious VM mouse brain homogenate was spiked into a background of meat and bone meal (MBM), digested with MC3, MC4 and used to infect VM mice as outlined below.

The method is designed to assess the ability of the proteases to inactivate TSEs in a protein-rich background. Such conditions are identical to those that would be encountered in meat rendering processes where the presence of TSE material in meat waste would be eliminated by treatment with protease. The results therefore demonstrate that the method of the invention is suitable for the large scale inactivation of TSE agents as a precursor to meat rendering, for the decontamination of infected meat waste or for other processes where inactivation of TSEs is required prior to further applications.

Preparation of Protease-Treated Infectious-MBH Spiked MBM and Controls

To evaluate the ability of proteases to inactivate infective material in a background of MBM samples were prepared and treated as follows:
2×100 mg aliquots of MBM were prepared in tubes
Add 700 µl of pH 12 buffer to each tube
Add 100 µl of infectious MBH dialysed to pH12 to each tube
Add 100 µl of protease solution (neat) to each tube
Heat at 60° C. for 30 minutes
Neutralise by addition of 100 µl of 10× phosphate buffer to each tube
Heat at 100° C. for 10 minutes
Allow samples to settle and draw off supernatant
Pool supernatant and mix, check pH is ~7.0 ~2 ml of infectivity test material ready for inoculation Preparation of Positive Control Sample Incorporating Protease Treated MBM Spiked with Untreated Infectious.

Positive controls were prepared in the presence of protease treated MBM to ensure that no toxic effects were observed as a combination of digested MBM and infectious material. Samples were prepared and treated as described below:

Digestion 1
4×100 mg aliquot of MBM in tubes
Add 700 µl of pH 12 buffer to each tube
Add 100 µl of protease solution (neat) to each tube
Heat at 60° C. for 30 minutes
Neutralise by addition of 90 µl of 10× phosphate buffer each tube
1. Heat at 100° C. for 10 minutes
2. Allow sample to settle and draw off supernatant (900 µl)
Digestion 2
100 µl of infectious MBH dialysed to pH12
Heat at 60° C. for 30 minutes
Neutralise by addition of 10 µl of 10× phosphate buffer
Heat at 100° C. for 10 minutes
Dilute sample with 890 µl PBS (1:10)
Take 100 µl of this sample and add 900 µl of supernatant from digestion 1 (1:100)
Check pH is ~7.0, ~1 ml of positive test material ready for inoculation Preparation of Material to Assess Toxicity of Protease Treated MBM Alone The toxicity of protease treated MBM in the absence of infectivity was assessed using MBM spiked with non-infectious MBH prior to treatment. Samples were prepared as described below:

1×100 mg aliquot of MBM in tube
Add 700 µl of pH 12 buffer
Add 100 µl of non-infectious MBH dialysed to pH12
Add 100 µl of protease solution (neat)
Heat at 60° C. for 30 minutes
Neutralise by addition of 100 µl of 10× phosphate buffer
Heat at 100° C. for 10 minutes
Allow sample to settle and draw off supernatant, check pH is ~7.0
~1 ml of toxicity/negative test material ready for inoculation Inoculation of VM Mice with Mouse Brain Homogenate.

VM mice were inoculated with 20 µl test material intracerebrally according to published methods. The test samples were MC3, MC4 and proteinase K treated infectious MBH in MBM (test groups), infectious MBH treated at pH 12, mixed with protease-treated MBM (positive control groups for each protease) and protease-treated non-infectious MBH in MBM (negative control).

TABLE 2

Table showing incubation period of VM mice infected with mouse brain homogenate (mbh) infected with BSE-301V spiked into a background of meat and bonemeal (MBM). Infectious mbh diluted in MBM was treated with MC3 or MC4, treated at pH 12 alone and mixed with protease digested MBM (positive controls). No toxicity was observed with protease digested MBM in the absence of infected material. The extension in incubation period of >31 days for MC3 and >38 days for MC4 both equate to greater than 4 log reduction in infectivity based on the MBH titration study described in the previous example.

| Treatment | No. of mice | First death | Last death (number of survivors) | Mean assuming any remaining mice are all sacrificed on current day | SD | Number of healthy mice; no clinical symptoms |
|---|---|---|---|---|---|---|
| MBM Study | | | | | | |
| MC3 positive | 15 | 153 | >192 (1) | 161.13 | 12.2 | 0 |
| MC3 | 25 | | >192 (24) | >192 | | 12 |
| MC4 positive | 15 | 143 | 158 | 148.13 | 4.36 | 0 |
| MC4 | 24 | | >186 (25) | >186 | | 25 |

The invention thus provides for the detection and degradation of TSE infectivity.

TABLE 3

| Organism | Domain | Growth | T opt | pH opt |
|---|---|---|---|---|
| Aeropyrum pernix | Archaeon | Aerobe | 95° C. | 7.0 |
| Alicyclobacillus acidocaldarius | Bacterium | Aerobe | 65° C. | 3.5 |
| Archaeoglobus fulgidus | Archaeon | Anaerobe | 85° C. | 6.5 |
| Bacillus caldotenax BT1 | Bacterium | Aerobe | 65° C. | 7 |
| Bacillus pallidus | Bacterium | Aerobe | 65° C. | 9.0 |
| Bacillus stearothermophilus L32-65 | Bacterium | Aerobe | 65° C. | 7.0 |
| Bacillus stearothermophilus LUDA T57 | Bacterium | Aerobe | 65° C. | 7.0 |
| Bacillus thermoproteolyticus Rokko | Bacterium | Aerobe | 65° C. | 7.0 |
| Bacillus sp. 11231 | Bacterium | Aerobe | 65° C. | 7.0 |
| Bacillus sp. 11276 | Bacterium | Aerobe | 65° C. | 7 |
| Bacillus sp. 11652 | Bacterium | Aerobe | 65° C. | 7 |
| Bacillus sp. 12031 | Bacterium | Aerobe | 65° C. | 7 |
| Desulfurococcus sp. | Archaeon | Anaerobe | 85° C. | 6.5 |
| Fervidobacterium pennivorans | Bacterium | Anaerobe | 70° C. | 8.5 |
| Hyperthermus butylicus | Archaeon | Anaerobe | 95° C. | 6.5 |
| Pyrococcus furiosus | Archaeon | Anaerobe | 95° C. | 7.5 |
| Pyrococcus horikoshii | Archaeon | Anaerobe | 95° C. | 7 |

TABLE 3-continued

| Organism | Domain | Growth | T opt | pH opt |
|---|---|---|---|---|
| *Sulfolobus acidocaldarius* 98-3 | Archaeon | Aerobe | 75° C. | 2.5 |
| *Sulfolobus hakonensis* | Archaeon | Aerobe | 75° C. | 2.5 |
| *Sulfolobus solfataricus* P1 | Archaeon | Aerobe | 75° C. | 2.5 |
| *Sulfolobus solfataricus* P2 | Archaeon | Aerobe | 75° C. | 2.5 |
| *Thermobrachium celere* | Bacterium | Anaerobe | 65° C. | 8.5 |
| *Thermococcus fumicolans* | Archaeon | Anaerobe | 85° C. | 6.5 |
| *Thermus caldophilus* GK24 | Bacterium | Aerobe | 70° C. | 8.0 |
| *Thermus aquaticus* YT1 | Bacterium | Aerobe | 70° C. | 8.0 |
| *Thermus* sp. 16132 | Bacterium | Aerobe | 70° C. | 8.0 |
| *Thermus* sp. 15673 | Bacterium | Aerobe | 70° C. | 8.0 |
| *Thermus* sp. Rt41A | Bacterium | Aerobe | 70° C. | 8 |

The invention claimed is:

1. A method for inactivating a transmissible spongiform encephalopathy (TSE) agent, located on or within infected apparatus or materials, or in clinical waste, said method comprising exposing the TSE agent to a thermostable proteolytic enzyme at an alkaline pH of from 8 to 13, wherein the exposing of the TSE agent to the thermostable proteolytic enzyme is carried out at a temperature that is 45° C. to less than 100° C., and the TSE agent is a prion.

2. The method of claim 1, wherein the pH is from 10 to 12.

3. The method of claim 1, wherein the TSE agent results in a disease is selected from the group consisting of Creutzfeld-Jacob disease; variant Creutzfeld-Jacob disease; Kuru; fatal familial insomnia; Gerstmann-Straussler-Scheinker syndrome; bovine spongiform encephalopathy; scrapie; feline spongiform encephalopathy; chronic wasting disease; and transmissible mink encephalopathy.

4. The method of claim 1, wherein the thermostable proteolytic enzyme is obtained from a thermophilic organism.

5. The method of claim 4, wherein the thermophilic organism is selected from the group consisting of *Thermotoga maritima; Thermotoga neopolitana; Thermotoga thermarum; Fervidobacterium islandicum; Fervidobacterium nodosum; Fervidobacterium pennivorans; Thermosipho africanus; Aeropyrum pernix; Thermus flavus; pyrococcus* spp.; *Sulfolobus solfataricus; Desulfurococcus; Bacillus thermoproteolyticus; Bacillus stearo-thermophilus; Bacillus* sp. 11231; *Bacillus* sp. 11276; *Bacillus* sp. 11652; *Bacillus* sp. 12031; *Thermus aquaticus; Thermus caldophilus; Thermus* sp. 16132; *Thermus* sp. 15673; and *Thermus* sp. Rt41A.

6. The method of claim 4 wherein the thermophilic organism is selected from the group consisting of archaea; hyperthermophilic bacteria and thermophilic bacteria.

7. The method of claim 1, wherein the thermostable proteolytic enzyme is selected from the group consisting of MC-A, MC-3 and MC-4.

8. The method of claim 1, wherein the pH is from 9 to 12.

9. The method of claim 1, wherein the pH is about 12.

10. The method of claim 1, wherein the exposing of the TSE agent to the thermostable proteolytic enzyme is carried out at a temperature that is about 60° C. to about 80° C.

11. The method of claim 1, wherein the TSE agent is a prion or a prion dimer.

12. The method of claim 1, further comprising exposing the TSE agent to the thermostable proteolytic enzyme and a detergent.

13. A method of claim 1, further comprising exposing the TSE agent to the thermostable proteolytic enzyme and an enzyme selected from the group consisting of proteases, lipases, peptidases, glycosylases, and nucleases.

14. A method of claim 1, further comprising exposing the TSE agent to the thermostable proteolytic enzyme and sonication.

15. The method of claim 1, wherein the temperature is 50° C. to less than 100° C.

16. The method of claim 15, wherein the temperature is between 55° C. and 85° C.

17. The method of claim 1, wherein the thermostable proteolytic enzyme is a serine protease.

18. The method of claim 1, wherein the thermostable proteolytic enzyme is a subtilisin.

19. The method of claim 18, wherein the thermostable proteolytic enzyme is a subtilisin derived from *Bacillus* bacteria.

20. The method of claim 19 wherein the thermostable proteolytic enzyme is a subtilisin derived from *Bacillus amyloliquefaciens, Bacillus lentus, Bacillus licheniformis, Bacillus subtilis* or is subtilisin PB92.

* * * * *